US009072701B2

(12) United States Patent
Hoffmann et al.

(10) Patent No.: US 9,072,701 B2
(45) Date of Patent: Jul. 7, 2015

(54) AVIAN INFLUENZA VIRUSES, VACCINES, COMPOSITIONS, FORMULATIONS, AND METHODS

(75) Inventors: Erich Hoffmann, Memphis, TN (US);
Scott L. Krauss, Millington, TN (US);
Mahesh Kumar, Fort Dodge, IA (US);
Richard J. Webby, Memphis, TN (US);
Robert G. Webster, Memphis, TN (US)

(73) Assignees: St. Jude Children's Research Hospital, Memphis, TN (US); Zoetis Services LLC, Florham Park, NJ (US)

( * ) Notice: Subject to any disclaimer, the term of this patent is extended or adjusted under 35 U.S.C. 154(b) by 0 days.

(21) Appl. No.: 11/737,104

(22) Filed: Apr. 18, 2007

(65) Prior Publication Data

US 2008/0118531 A1    May 22, 2008

Related U.S. Application Data

(60) Provisional application No. 60/794,054, filed on Apr. 21, 2006.

(51) Int. Cl.
| A61K 49/00 | (2006.01) |
| A01N 63/00 | (2006.01) |
| A61K 39/12 | (2006.01) |
| A61K 39/145 | (2006.01) |
| A61K 47/00 | (2006.01) |
| C07K 14/005 | (2006.01) |
| A61K 35/12 | (2015.01) |
| A61K 39/39 | (2006.01) |
| A61K 39/00 | (2006.01) |

(52) U.S. Cl.
CPC ............. A61K 39/145 (2013.01); C07K 14/005 (2013.01); A61K 49/0004 (2013.01); A61K 35/12 (2013.01); A61K 39/39 (2013.01); A61K 2039/5252 (2013.01); A61K 2039/552 (2013.01); A61K 2039/55566 (2013.01); C12N 2760/16134 (2013.01); A61K 39/12 (2013.01); A61K 2039/70 (2013.01)

(58) Field of Classification Search
CPC .................... A61K 39/145; A61K 2039/5254; A61K 2039/6075; C12N 2760/16134; C12N 2760/16151; C12N 2760/16234; C12N 2760/16222; C12N 15/86; C12N 2760/16251; C12N 2760/16121; C12N 2760/16034; C12N 2760/16111; C12N 2760/16262; C12N 2760/18534; C12N 2710/10322; C12N 2710/10343; C12N 2710/24134; C12N 2710/24151; C12N 2720/12121; C12N 2720/12134; C12N 2760/12034; C12N 2760/12051; C12N 2760/16011; C12N 2760/16022; C12N 2760/16061
See application file for complete search history.

(56) References Cited

U.S. PATENT DOCUMENTS

| 2002/0164770 | A1 | 11/2002 | Hoffmann |
| 2004/0029251 | A1 | 2/2004 | Hoffman et al. |
| 2005/0054846 | A1 | 3/2005 | Webster et al. |
| 2005/0158342 | A1 | 7/2005 | Kemble et al. |
| 2006/0204976 | A1 | 9/2006 | Plana-Duran et al. |
| 2007/0231348 | A1* | 10/2007 | Kawaoka et al. .......... 424/209.1 |

FOREIGN PATENT DOCUMENTS

| WO | WO 01/22992 | * | 4/2001 |
| WO | WO-01/83794 A2 | | 11/2001 |
| WO | WO-03/086453 A1 | | 10/2003 |

OTHER PUBLICATIONS

FDA News Release, FDA Approves First U.S. Vaccine for Humans Against the Avian Influenza Virus H5N1, 2007, downloaded from <http://www.fda.gov/NewsEvents/Newsroom/PressAnnouncements/2007/ucm108892.htm> on Jun. 7, 2009.*
FDA Approval Letter to Sanofi Pasteur Inc., Apr. 17, 2007 Approval Letter—Influenza Virus Vaccine, H5N1, 2007, downloaded from <http://www.fda.gov/BiologicsBloodVaccines/Vaccines/ApprovedProducts/ucm112838.htm> on Jun. 7, 2009.*
Genbank Accession # AAS79359, hemagglutinin [Influenza A virus (A/muscovy duck/Vietnam/MdGL/2004 (H5N1))], Published May 24, 2005.*
Cajavec et al., Tween 80-Solubilized Newcastle Disease Virus Prepared as a Water-in-Oil-in-Water Vaccine, 1996, Avian Diseases, vol. 40, pp. 193-201.*
Hoffmann et al., Role of specific hemagglutinin amino acids in the immunogenicity and protection of H5N1 influenza virus vaccines, 2005, PNAS, vol. 102, No. 36, pp. 12915-12920.*
Air, G. M. et al., "The Neuraminidase of Influenza Virus," Proteins: Structure, Function, and Genetics, Alan R. Liss, Inc., 1989, 6:341-356.
Air, G. M., "Sequence Relationships Among the Hemagglutinin Genes of 12 Subtypes of Influenza A Virus," Proceedings of the National Academy of Sciences U.S.A., 1981, 78(12):7639-7643.

(Continued)

Primary Examiner — Benjamin P Blumel
(74) Attorney, Agent, or Firm — Scully, Scott, Murphy & Presser, P.C.

(57) ABSTRACT

A vaccine composition and method which is effective in preventing or ameliorating Avian Influenza Virus infection is set forth herein. The vaccine contains at least two inactivated strains of avian influenza virus, wherein the combined hemagglutinin (HA) total is at least about 200 HA/dose of the vaccine composition, and wherein each of the strains presents at least about 128 HA/dose, and further wherein one of the strains has the same HA subtype as that of a challenge virus, and wherein at least one of the strains has a different NA subtype than the challenge virus.

11 Claims, 1 Drawing Sheet

(56) References Cited

OTHER PUBLICATIONS

Capua, I. et al., "Development of a DIVA (Differentiating Infected from Vaccinated Animals) Strategy Using a Vaccine Containing a Heterologous Neuraminidase for the Control of Avian Influenza," Avian Pathology, 2002, 32:1, 47-55.
Claas, E. C. J. et al., "Human Influenza A H5N1 Virus Related to a Highly Pathogenic Avian Influenza Virus," The Lancet, 1998, 351:472-477.
Cox, N. J. et al., "Influenza," The Lancet, 1999, 354:1277-1282.
Ellis, T. M. et al., "Vaccination of Chickens Against H5N1 Avian Influenza in the Face of an Outbreak Interrupts Virus Transmission," Avian Pathology, 2004, 33(4):405-412.
Fodor, E. et al., "Rescue of Influenza A Virus from Recombinant DNA," Journal of Virology, Nov. 1999, 73(11):9679-9682.
Fouchier, R. et al., "Global Task Force for Influenza," Nature, May 26, 2005, 419-420.
Gao, W. et al., "Protection of Mice and Poultry from Lethal H5N1 Avian Influenza Virus through Adenovirus-Based Immunization," Journal of Virology, Feb. 2006, 80(4):1959-1964.
Ha, Y. et al., "X-ray Structures of H5 Avian and H9 Swine Influenza Virus Hemagglutinins Bound to Avian and Human Receptor Analogs," Proceedings of the National Academy of Sciences U.S.A., Sep. 25, 2001, 98(20):11181-11186.
Halvorson, D. A., "The Control of H5 or H7 Mildly Pathogenic Avian Influenza: A Role for Inactivated Vaccine," Avian Pathology, 2002, 31:1, 5-12.
Hoffmann, E. et al., "Eight-plasmid System for Rapid Generation of Influenza Virus Vaccines," Vaccine, 2002, 20:3165-3170.
Hoffmann, E. et al, "A DNA Transfection System for Generation of Influenza A Virus from Eight Plasmids," Proceedings of the National Academy of Sciences U.S.A., May 23, 2000, 97(11):6108-6113.
Kuiken, T. et al., "Avian H5N1 Influenza in Cats," Science, Oct. 8, 2004, 306:241.
Lee, C. et al., "Generation of Reassortant Influenza Vaccines by Reverse Genetics that allows Utilization of a DIVA (Differentiating Infected from Vaccinated Animals) Strategy for the Control of Avian Influenza," Vaccine, 2004, 22:3175-3181.
Krug, R. M. et al., "The Influenza Viruses," R.M. Krug, ed., Plenum Press, New York, 1989, pp. 1, 2, 89-152.
Li, K. S. et al., "Genesis of Highly Pathogenic and Potentially Pandemic H5N1 Influenza Virus in Eastern Asia," Letters to Nature, Nature, Jul. 8, 2004, 430:209-213.
Liu, M. et al., "Preparation of a Standardized, Efficacious Agricultural H5N3 Vaccine by Reverse Genetics," Virology, 2003, 314:580-590.
Luschow, D. et al., "Protection of Chickens from Lethal Avian Influenza A Virus Infection by Live-virus Vaccination with Infectious Laryngotracheitis Virus Recombinants Expressing the Hemagglutinin (*H5*) Gene," Vaccine, 2001, 19:4249-4259.
Naeem, K., "The Avian Influenza H7N3 Outbreak in South Central Asia," Proceedings of the 4th International Symposium on Avian Influenza, Athens, Georgia, USA, 1998, pp. 31-35.
Neumann, G. et al., "Generation of influenza A viruses entirely from cloned cDNAs," Proceedings of the National Academy of Sciences U.S.A., 1999, 96:9345-9350.
Neumann, G. et al., "Genetic Engineering of Influenza and Other Negative-Strand RNA Viruses Containing Segmented Genomes," Advances in Virus Research, 1999, 53:265-300.
Nicholson, K. G. et al., "Safety and antigenicity of non-adjuvanted and MF59-adjuvanted influenza A/Duck/Singapore/97 (H5N3) vaccine: a randomised trial of two potential vaccines against H5N1 influenza," The Lancet, 2001, 357:1937-1943.
Palese, P. et al., "Development of Novel Influenza Virus Vaccines and Vectors," The Journal of Infectious Diseases, 1997,176 (Suppl. 1):S45-9.
Palese, P. et al., "Negative-strand RNA viruses: Genetic engineering and applications," Proceedings of the National Academy of Sciences U.S.A., 1996, 93:11354-11358.
Qiao, C. et al., "Protection of chickens against a highly lethal H5N1 and H7N1 avian influenza viruses with a recombinant fowlpox virus co-expressing H5 haemagglutinin and N1 neuraminidase genes," Avian Pathology, 2003, 32:1, 25-31.
Scholtissek, C. et al., "The Nucleoprotein as a Possible Major Factor in Determining Host Specificity of Influenza H3N2 Viruses," Virology, 1985, 147, 287-294.
Shortridge, K., "Poultry and the influenza H5N1 outbreak in Hong Kong, 1997: Abridged chronology and virus isolation," Vaccine, 1999, 17:S26-S29.
Stephenson, I. et al., "Boosting immunity to influenza H5N1 with Mf59-adjuvanted H5N3 A/Duck/Singapore/97 vaccine in a primed human population," Vaccine, 2003, 21:1687-1693.
Stephenson, I. et al., "Cross-Reactivity to Highly Pathogenic Avian Influenza H5N1 Viruses after Vaccination with Nonadjuvanted and MF59-Adjuvanted Influenza A/Duck/Singapore/97 (H5N3) Vaccine: A Potential Priming Strategy," Journal of Infectious Diseases, 2005, 191:1210-1215.
Suarez, D. L. et al., "Comparisons of Highly Virulent H5N1 Influenza A Viruses Isolated from Humans and Chickens from Hong Kong," Journal of Virology, 1998, 72:6678-6688.
Subbarao, K. et al., "Characterization of an Avian Influenza A (H5N1) Virus Isolated from a Child with a Fatal Respiratory Illness," Science, 1998, 279:393-396.
Subbarao, K. et al., "Evaluation of a Genetically Modified Reassortant H5N1 Influenza A Virus Vaccine Candidate Generated by Plasmid-Based Reverse Genetics," Virology, 2003, 305:192-200.
Suzuki, Y. et al., "Origin and Evolution of Influenza Virus Hemagglutinin Genes," Molecular Biological Evolution, 2002, 19(4):501-509.
Swayne, D. E., "Highly pathogenic avian influenza," Review of Science and Technology of the Office of International Epiz., 2000, 19(2):463-482.
Takada, A. et al., "Avirulent Avian Influenza Virus as a Vaccine Strain against a Potential Human Pandemic," Journal of Virology, 1999, 73:8303-8307.
Tian, G. et al. "Protective efficacy in chickens, geese and ducks of an H5N1-inactivated vaccine developed by reverse genetics," Virology, 2005, 341:153-162.
Van Der Goot, J. A. et al., "Quantification of the effect of vaccination on transmission of avian influenza (H7N7) in chickens," Proceedings of the National Academy of Sciences of the U.S.A., 2005, 102:18141-18146.
Wharton, S. A. et al., "Structure, Function, and Antigenicity of the Hemagglutinin of Influenza Virus," published in The Influenza Viruses, R.M. Krug, editor, Plenum Press, New York, 1989, pp. 153-174.
Govorkova et al., Genbank Accession # AAW80718, Feb. 9, 2005.
Webby et al., Genbank Accession # AAO62036, Oct. 29, 2004.
The World Health Organization Global Influenza Program Surveillance Network, "Evolution of H5N1 Avian Influenza Viruses in Asia", Emerging Infectious Diseases, 11(10):1515-1521 (2005).

* cited by examiner

```
                           10        20        30        40        50        60        70
                       ....|....|....|....|....|....|....|....|....|....|....|....|....|....|
H5_goose_HK_437        dqiciqyhannsteqvdtimeknvtvthaqdilekthngklcdldgvkplilrdcsva:wllqrpmcdef
H5_chicken_VN_c58      ......................................................................

80        90       100       110       120       130       140
                       ....|....|....|....|....|....|....|....|....|....|....|....|....|....|
H5_goose_HK_437        invpewsyivekaspandlcypgdfnnyeelkhllsrtnhfekiqiipksswsnhdass:vssacpyh.k
H5_chicken_VN_c58      ...............N.V..........D...........I................S.E..L........Q.

150       160       170       180       190       200       210
                       ....|....|....|....|....|....|....|....|....|....|....|....|....|....|
H5_goose_HK_437        ssffrnvvwlikknsayptikrsynntnqedllvlwgihhpndaaeqtklyqnpttyisvctstlnqrlv
H5_chicken_VN_c58      ................T.....................................................

220       230       240       250       260       270       280
                       ....|....|....|....|....|....|....|....|....|....|....|....|....|....|
H5_goose_HK_437        peiatrpkvnqqsqrmeffwtilkpndainfesngnfiapeyaykivkkgdsaimkseleygncntkcqt
H5_chicken_VN_c58      .R....S.................R......................T...........A....

290       300       310       320       330       340       350
                       ....|....|....|....|....|....|....|....|....|....|....|....|....|....|
H5_goose_HK_437        pmgainssmpfhnihpltigecpkyvksnrlvlatglrntpqietrglfgaiagfiecgwqgmvdcwygy
H5_chicken_VN_c58      .............................................S......................

360       370       380       390       400       410       420
                       ....|....|....|....|....|....|....|....|....|....|....|....|....|....|
H5_goose_HK_437        hhsneqgsgyaadkestqkaidgvtnkvnsiidkmntqfeavgrefnnlerrienlnkkmedgtldvwty
H5_chicken_VN_c58      ......................................................................

430       440       450       460       470       480       490
                       ....|....|....|....|....|....|....|....|....|....|....|....|....|....|
H5_goose_HK_437        naellvlmenertldfhdsnaknlydkvrlqlrdnakelgngcfefyhkcdnecmesvkn:tydypqyse
H5_chicken_VN_c58      .......................V...........................R............

500       510       520       530       540
                       ....|....|....|....|....|....|....|....|....|....|....|...
H5_goose_HK_437        earlnreeisqvklesmgtyqilsiystvasslalaimvaglslwmcsnqslqcrici
H5_chicken_VN_c58      ....K..........I.I..........V............................
```

AVIAN INFLUENZA VIRUSES, VACCINES, COMPOSITIONS, FORMULATIONS, AND METHODS

CROSS REFERENCE TO RELATED APPLICATIONS

This application claims priority under 35 U.S.C. §119(e) to U.S. provisional patent application Ser. No. 60/794,054, filed Apr. 21, 2006, which application is incorporated by reference herein in its entirety.

BACKGROUND OF THE INVENTION

1. Technical Field of the Invention

The present invention relates generally to influenza vaccines, more specifically to avian influenza vaccines and formulations thereof useful for vaccinating susceptible avian species. The invention also relates to new methods for preventing or ameliorating avian influenza viral disease in poultry.

2. Description of the Related Art

Influenza viruses, most notably particular strains of A and B virus, are a serious cause of morbidity and mortality throughout the world, resulting in annual disease outbreaks. Periodically but at irregular intervals pandemics occur and result in particularly high levels of illness and death. Pandemics are historically the result of novel virus subtypes of influenza A, created by reassortment of the segmented genome (antigenic shift), whereas annual epidemics are generally the result of evolution of the surface antigens of influenza A and B virus (antigenic drift). Human influenza viruses often originate from avian strains of influenza virus so that influenza infection is at its basis a zoonosis. There is also evidence that swine can serve as an intermediate host ("mixing vessel") for the generation of new avian-originated strains that are pathogenic in humans (Scholtissek et al., Virology 1985, 147:287). The H5N1 influenza A outbreak in Hong Kong in 1997 showed that highly pathogenic influenza A viruses can also be transmitted directly from avian species to humans (Claas et al., Lancet 1998, 351:472; Suarez et al., J. Virol. 1998, 72:6678; Subbarao et al., Science 1998, 279:393; Shortridge, Vaccine 1999, 17 (Suppl. 1): S26-S29). In 2003, the H5N1 viruses in Southeast Asia comprised different co-circulating geneotypes, but in 2004 a single genotype, known as the "Z-genotype", became dominant (Li et al., Nature 2004, 430: 209).

Current evidence indicates that fatal human cases resulted from the direct transmission of this genotype from birds to humans and that it also infected cats, with direct cat to cat transmission (Kuiken et al., Science 2004, 306:241). This and other evidence of the changing host range and widespread distribution of this virus raised concern that H5N1 viruses may acquire the characteristics that allow transmission from human to human. Humans would have no immunity to such new H5N1 viruses, which could cause catastrophic pandemic influenza (Fouchier et al., Nature 2005, 435:419). The potential of influenza A viruses to generate new pathogenic strains from a vast number of circulating strains in animal reservoirs indicates that disease control requires monitoring these viruses and developing improved antiviral therapies and vaccines. The speed with which new viral strains develop demands vigilance in this monitoring effort, including improved techniques for assessing the efficacy of vaccines to novel strains.

Avian Influenza, also called "AI," is an acute and highly contagious viral infection of chickens and other fowl. As an influenza virus, it is classified in subtypes on the basis of antigen differences in the hemagglutinin (HA; also may be abbreviated as H) and neuraminidase (NA; also may be abbreviated as N) molecules, which "reassort" or "mutate" from season to season. Because the virus constantly mutates, it vaccine preparation is difficult due to the unpredictability as to which strain will reappear in subsequent seasons. The strains used for vaccine preparation often do not reproduce under manufacturing conditions at a very fast rate, so that waiting for an appearance of a particular strain, and then manufacturing the correct vaccine to protect against the strain does not provide a viable option. Typically, the epidemic of the particular strain will last for several months, and then perhaps disappear for several years.

Influenza viruses are classified into various A, B, and C topologies, according to the virus' group antigen. Influenza viruses of the A, B, and C types are distinguishable on the basis of antigenic differences in viral nucleocapsid (NP) and matrix (M) proteins. A-type influenza viruses are classified into subtypes on the basis of such differences in hemagglutinin (HA) and neuraminidase (NA). Nine subtypes of the neuraminidase NA proteins, designated NA 1 to NA 9, and fifteen different subtypes of the serum hemagglutinin HA proteins, designated HA 1 to HA 15, have been identified. In birds, viruses carrying each of the various HA (or H) and NA (or N) subtypes have been isolated.

Influenza A, B and C, of the family Orthomyxoviridae, all have a segmented negative strand RNA genome that is replicated in the nucleus of the infected cell, has a combined coding capacity of about 13 kb, and contains the genetic information for ten viral proteins. Specifically, influenza viruses have eight negative-sense RNA (nsRNA) gene segments that encode at least 10 polypeptides, including RNA-directed RNA polymerase proteins (PB2, PB1 and PA), nucleoprotein (NP), neuraminidase (NA), hemagglutinin (HA, which after enzymatic cleavage is made up of the association of subunits HA1 and HA2), the matrix proteins (M1 and M2) and the non-structural proteins (NS1 and NS2) (Krug et al., In The Influenza Viruses, R. M. Krug, ed., Plenum Press, New York, 1989, pp. 89-152).

Recently developed reverse-genetics systems have allowed the manipulation of the influenza viral genome (Palese et al., Proc. Natl. Acad. Sci. USA 1996, 93:11354; Neumann and Kawaoka, Adv. Virus Res. 1999, 53:265; Neumann et al., Proc. Natl. Acad. Sci. USA 1999, 96:9345; Fodor et al., J. Virol. 1999, 73:9679). For example, it has been demonstrated that the plasmid-driven expression of eight influenza nsRNAs from a pol I promoter and the coexpression of the polymerase complex proteins result in the formation of infectious influenza A virus (Hoffmann et al., Proc. Natl. Acad. Sci. USA 2000, 97:6108).

The virus particle of the influenza virus has a size of about 125 nm and consists of a core of negative sense viral RNA associated with the nucleoprotein, surrounded by a viral envelope with a lipid bilayer structure. The inner layer of the viral envelope is composed predominantly of matrix proteins and the outer layer contains most of the host-derived lipid material. The so-called "surface proteins", neuraminidase (NA) and hemagglutinin (HA), appear as spikes on the surface of the viral body. Infectivity of novel influenza viruses depends on the cleavage of HA by specific host proteases, whereas NA is involved in the release of progeny virions from the cell surface and prevents clumping of newly formed virus.

The HA and NA proteins embedded in the viral envelope are the primary antigenic determinants of the influenza virus (Air et al., Structure, Function, and Genetics, 1989, 6:341-356; Wharton et al., In The Influenza Viruses, R. M. Krug, ed., Plenum Press, New York, 1989, pp. 153-174). Due to reassortment of influenza segmented genome, new HA and NA variants are constantly created for which a newly infected organism has no anamnestic immune response. HA glycoprotein is the major antigen for neutralizing antibodies and is involved in the binding of virus particles to receptors on host cells.

HA molecules from different virus strains show significant sequence similarity at both the nucleic acid and amino acid levels. This level of similarity varies when strains of different subtypes are compared, with some strains clearly displaying higher levels of similarity than others (Air, Proc. Natl. Acad. Sci. USA, 1981, 78:7643). The levels of amino acid similarity vary between virus strains of one subtype and virus strains of other subtypes (Air, Proc. Natl. Acad. Sci. USA, 1981, 78:7643). This variation is sufficient to establish discrete subtypes and the evolutionary lineage of the different strains, but the DNA and amino acid sequences of different strains are still readily aligned using conventional bioinformatics techniques (Air, Proc. Natl. Acad. Sci. USA, 1981, 78:7643; Suzuki and Nei, Mol. Biol. Evol. 2002, 19:501).

HA is a viral surface glycoprotein comprising approximately 560 amino acids and representing 25% of the total virus protein. It is chiefly responsible of adhesion of the viral particle to and its penetration into a host cell in the early stages of infection. Among the viral proteins, hemagglutinin is most subject to post-translational rearrangement. After synthesis of hemagglutinin has been completed, the molecule follows the exocytotic pathway of the host cell, in the course of which HA is folded, assembled in trimers and glycosylated. Finally, HA is cleaved into two subunits Hi and H2; which activates the molecule and promotes the virion's infective capacity.

Differences in the sequence of basic amino acids within the cleavage site correlates with the capacity of the avian influenza virus to produce localized, symptomatic infections or generalized infections having a lethal outcome for many avian species. It has therefore been suggested that this feature might be important in influencing the virus' organ-tropism, host specificity, as well as its pathogenicity. With respect to the pathogenicity of the virus, strains with multibase-site HA find proteases that cleave the HO molecule, in the active form H1 and H2 in several cellular types thus giving rise to multiple infection cycles with a massive production of infectious viral particles and causing a generalization of the infections in all of the districts within a short time period (HPAI strains). The infection will consequently turn out to have an acute-hyperacute course, with very high mortality.

Neuraminidase (NA) is a second membrane glycoprotein of the influenza A viruses. NA is a 413 amino acid protein encoded by a gene of 1413 nucleotides. NA participates in the destruction of the cellular receptor for the viral hemagglutinin by cleaving between the sialic acid molecule and the hemagglutinin itself. In this way it believed to be possible to ease liberation of viral progeny by preventing newly formed viral particles from accumulating along the cell membrane as well as by promoting transportation of the virus through the mucus present on the mucosal surface. NA is an important antigenic determinant that is subject to antigenic variations.

The influenza vaccines currently licensed by public health authorities for use in the United States and Europe are inactivated influenza vaccines as well as the live attenuated FLU-MIST vaccine in the United States. Viruses presenting epidemiologically important influenza A and influenza B strains are grown in embryonated chicken eggs and the virus particles are subsequently purified and inactivated by chemical means to form vaccine stocks. Each year the WHO selects subtypes which most likely will circulate for that year for vaccine development.

Although influenza vaccines have been in use since the early 1940's for human vaccination and since the late 1960's for equine vaccination, the existence of extensive animal reservoirs, combined with the threat of emergence of a novel influenza virus capable of causing a pandemic, has spurred research into novel therapies with which to fight the virus. Several important advances in the field of influenza have occurred in the last few years (reviewed in Cox and Subbarao, Lancet 1999, 354:1277-82). For example, an experimental live, attenuated, intranasally administered trivalent influenza vaccine was shown to be highly effective in protecting young children against influenza A H3N2 and influenza B. Other approaches to improve the efficacy of the current (killed) influenza virus vaccines include the generation of cold-adapted and genetically engineered influenza viruses containing specific attenuating mutations (reviewed in Palese et al., J. Infect. Dis., 1997, 176 Suppl 1:S45-9). It is hoped that these genetically altered viruses, in which the HA and NA genes from circulating strains have been incorporated by reassortment, can be used as safe live influenza virus vaccines to induce a long-lasting protective immune response in humans. Although cold-adapted vaccines appear to be efficacious in children and young adults, they may be too attenuated to stimulate an ideal immune response in elderly people, the major group of the 20000-40000 individuals in the USA dying each year as a result of influenza infection.

Readily available vaccines would provide the most effective tool against emergent pandemic influenza. After the 1997H5N1 outbreak in Hong Kong, vaccines produced by two different approaches were tested in humans. Conventional subunit H5 vaccine produced from A/duck/Singapore/3/97 was poorly immunogenic in humans, even against antigenically closely related strains and after multiple vaccination (Nicholson et al., Lancet 2001, 357:1937; Stephenson et al., Journal of Infectious Disease 2005, 191: 1210). The use of the adjuvant MF59 increased the antibody titer of this H5 vaccine (Stephenson et al., Vaccine 2003, 21:1687). Vaccination with inactivated "split" vaccine derived from nonpathogenic A/duck/HK/836/80 (H3N1) virus and the modified H5 hemagglutinin from A/HK/156/97 (H5N1) virus induced barely detectable titers of neutralizing antibodies (Takada et al., Journal of Virology 1999, 73:8303). Thus, although these H5N1 vaccines were well tolerated, they appeared to be poorly immunogenic. The current lack of effective vaccines against H5N1 virus strains increases the threat of these viruses to cause pandemic disease.

Serum antibody titer methods are the accepted surrogate measures of immune protection after vaccination or viral infection. The predominantly used serum antibody titer methods are virus neutralization titer assays and hemagglutinin inhibition (HI) titer assays. These assays are based on the ability of influenza antibodies from human serum to cross react with antigens under in vitro conditions. Assays are selected for a given situation based not only on their ability to provide consistent and applicable results but also based on their ease of use and the facility requirements for each type of assay.

Briefly stated, the virus neutralization assay examines the ability of antibodies from a serum sample to block the infection of cultured cells by influenza virus. The assay is carried out by creating serial dilutions (titers) of a serum sample and combining each of these dilutions with a standard amount of infectious virus. Each dilution mixture is then presented to a defined cell culture and the resulting infection rates assayed.

The virus neutralization titer assay is considered to be an extremely useful and reliable test to examine the level of immunoprotective antibodies present in a given individual. It is, however, dependent on specialized cell culture facilities and therefore is not universally available. The methodology is also laborious and time consuming hence poorly suited to screening large numbers of samples.

The hemagglutinin inhibition (HI) assay similarly examines the ability of antibodies from a serum sample to bind with a standardized reference virus. The basis for this assay is the fact that influenza viruses will bind to and agglutinate erythrocytes. In the HI assay, serial dilutions of serum sample are mixed with standard amounts of reference virus and after a set incubation period added to erythrocytes. The association between reference viruses and erythrocytes into complexes is then detected visually. The highest dilution of serum that inhibits hemagglutinin is read as the hemagglutinin inhibition titer. Although not as sensitive of vaccine immunogenicity as other assays, the HI assay is widely employed due to its relatively simple technology and laboratory requirements.

The current Asian H5N1 highly pathogenic avian influenza has spread over much of Asia and into Europe and Africa. As well as affecting village and commercial chicken operations in many South East Asian countries, it differs from past H5 avian influenzas in that it causes morbidity and mortalities in other domesticated birds, such as ducks and turkeys and in wild waterbirds. Effective vaccines that can prevent infection, as well as disease, and be used in a variety of avian species are needed for field use.

The major control strategy for highly pathogenic avian influenza (HPAI) outbreaks in poultry has traditionally been one of eradication via movement restrictions and slaughter of affected and at-risk birds. With the widespread presence, however, of the current Asian H5N1 virus in village poultry, including ducks and turkeys, and in wildlife species, particularly migrating birds, alternate control strategies must be considered, with vaccines likely to be a key component.

Currently available commercial vaccines for avian influenza are oil emulsion killed virus vaccines that have mostly been used to control endemic low pathogenic avian influenza (LPAI) in chickens and turkeys, or HPAI outbreaks in Pakistan and Mexico. Halvorson, *Avian Path.* 31:5-12 (2002); Naeem, *Proceedings of the 4th International Symposium on Avian Influenza* 31-35. (Athens, Ga., USA, 1998); Swayne and Suarez, *Rev. Sci. Tech. Off. Int. Epiz.* 19:463-482 (2000). Both killed vaccines and recombinant fowlpox vaccines are currently used to control mildly pathogenic avian influenza in Mexico. Id. The European Union has approved use of inactivated oil emulsion vaccines for use in Italy, provided they allow for differentiation of vaccinated versus infected birds. Capua et al., *Avian Path.* 32:47-55 (2002).

While it has been demonstrated that an inactivated oil emulsion vaccine could interrupt transmission of H7N7 (Van der Goot et al., *Proc. Natl. Acad. Sci. U.S.A.* 102:18141-18146 (2005)) or the current H5N1 HPAI (Ellis et al., *Avian Path.* 33:405-412 (2004)), concerns still exist that these vaccines may not have 100% efficacy in the field and will not totally prevent shedding of virus. Additionally, their use does not allow the differentiation between vaccinated and infected birds, which interferes with monitoring the disease status within flocks and regions; nor have they been formulated or tested for vaccination efficacy in ducks.

The Asian H5N1 virus cannot be grown to high titer in eggs, which is the traditional method of virus production for human and avian influenza vaccines. Thus, alternatives to homologous virus vaccines are being developed. Live vectored vaccines can provide additional safety and the ability to differentiate between infected and vaccinated birds.

Fowlpox virus (Qiao et al., *Avian Path.* 32:25-31 (2003), infectious laryngotracheitis virus (Luschow et al., *Vaccine* 19:4249-4259 (2001) and adenovirus (Gao et al., *J. Virol.* 80:1959-1964 (2006)) vectors expressing H5 have all been assessed and shown to have protective efficacy, with reduction, but not complete elimination, of virus shedding. Other influenza strains, particularly those that share the H5 hemagglutinin type, but with a different neuraminidase, have been shown to have some efficacy in the field (Ellis et al., *Avian Path.* 33:405-412 (2004)), but the most promising approach is the use of reverse genetics to create an influenza virus that has the current H5 in a genetic background that allows growth to high titer in eggs, but has low pathogenicity in either avian or mammalian species.

Reverse genetics has been used to create influenza virus reassortants with the hemagglutinin and neuraminidase genes from either the human H5N1 isolate, A/HK/491/97 (Subbarao et al., *Virol.* 305:192-200 (2003)), or the avian H5N1 isolate, A/Goose/Guangdong/96 (Tian et al., *Virol.* 341:153-162 (2005). Both of these reassortants are apathogenic in chickens and the reassortant virus with H5 and N1 from A/Goose/Guangdong/96 has been tested as a formalin inactivated preparation for protective efficacy against the parent HPAI H5N1 in specific pathogen free (SPF) chickens, and in non-SPF geese and ducks. Those studies demonstrated that the reassortant vaccine could prevent mortality and reduce shedding of the challenge virus.

Inclusion of a different neuraminidase subtype in the reassortant vaccine allows differentiation of infected from vaccinated birds. This principle has been demonstrated with reassortants using hemagglutinin genes from H5 and H7 LPAI viruses and the remaining genes, including the N1 from A/WSN/33 (Lee et al., *Vaccine* 22:3175-3181 (2004)). Oil emulsion vaccines with these reassortants reduced replication of the parental H5 and H7 LPAI strains in SPF chickens. A reassortant virus with H5 from A/Goose/Hong Kong/437-4/99 and N3 from A/Duck/Germany/1215/73 has been constructed (Liu et al., *Virol.* 314:580-590 (2003)). When formulated as an oil emulsion, the vaccine was able to protect SPF chickens against mortality following challenge with HPAI H5N1 virus. At appropriate doses of the vaccine, there was no challenge viruses detected in the birds.

Reverse genetics influenza vaccines have been postulated to be utilizable in these "DIVA" methods, where a vaccine is administered having an N different from the viral strain against which the bird is being vaccinated thereby facilitating the differentiation of vaccinated animals from infected birds. Published PCT WO 03/086453, which is incorporated by reference in its entirety herein, describes the DIVA technology, and some representative vaccines utilizable in the methods thereof.

Reverse genetics vaccines offer a number of obvious advantages over conventional vaccines prepared from naturally occurring virus strains. Through reverse genetics technology, specific genes from virus A may be replaced with the corresponding gene from virus B. Additionally, these genes may be modified to reduce viral pathogenicity while retaining the resulting vaccine's protective properties.

Vaccines based on the current Asian H5N1 strain and which overcome these problems and for use in a variety of poultry species are urgently needed that provide an alternative to eradication of infected flocks. A requirement of such avian influenza virus vaccines is that they (a) elicit a rapid immune response in the vaccinated avian and (b) enable differentiation of vaccinated birds from infected birds. Thus, there remains a need for improved avian influenza vaccines which not only invoke a rapid immune response, and a higher titer response, but which also produce a sterilizing effect, preventing the growth, shedding and transmission of a challenge virus to other susceptible species.

SUMMARY OF THE INVENTION

The present invention fulfills these and other related needs by providing reassorted avian influenza viruses and avian influenza vaccines, compositions comprising one or more avian virus and/or vaccine, formulations thereof, and methods for the use of inventive avian viruses and/or vaccines, compositions, and/or formulations, wherein the viruses and vaccines comprise an HA gene derived from a highly pathogenic avian influenza virus, an NA gene derived from a low pathogenicity avian influenza virus, and a viral backbone comprising the remaining avian influenza virus genes from a low pathogenicity avian influenza virus.

Low pathogenicity avian influenza viruses and vaccines disclosed herein are effective in preventing or ameliorating avian influenza, and provide the additional benefit that they prevent the growth, shedding and/or transmission of the challenge influenza virus to other species. Thus, low pathogenicity avian influenza viruses and vaccines of the present invention comprise an HA portion derived from a first highly pathogenic strain of H5 avian influenza, an NA portion derived from a second low pathogenic strain which has an N subtype different from that of the virus from which the HA portion is derived, and the remaining viral genome selected from a low pathogenic virus which may be the same or different than the virus from which the N portion is derived.

Within certain embodiments, the HA portion is derived from a highly pathogenic strain of H5 avian influenza exemplified herein by the Asian strain of H5N1 designated A/chicken/Vietnam/C58/04. Within other embodiments, the NA portion is derived from a second low pathogenic strain which has an NA subtype different from that of the virus from which the HA portion is derived. Typically, the NA subtype is from a European or American lineage strain having an N3, N5 or N9 subtype. Exemplified herein are reassortant H5N3 avian influenza viruses wherein the N3 gene is derived from the low pathogenic H2N3 avian influenza strain designated A/DK/Germany/1215/73. Within still further embodiments, the remaining viral genome is selected from a low pathogenic virus exemplified herein by the low pathogenic avian influenza virus designated A/Puerto Rico/8/34 H1N1.

Thus, exemplified herein are reassortant H5N3 avian influenza viruses and vaccines comprising an HA H5 gene from the recent pathogenic Asian outbreak strain A/Ck/Vietnam/C58/04 (H5N1); an NA N3 gene from the low pathogenicity strain A/DK/Germany/1215/73 (H2N3), which facilitates differentiation from the wild type infection (N1); and an avian influenza backbone from the low pathogenicity strain A/Puerto Rico/8/34 (H1N1), which is a well-characterized and safe virus having no pathogenic effects in either humans or animals. The methodology for constructing an H5N3 reverse genetics virus is described in detail in Published PCT WO 01/083794, which disclosure is incorporated herein by reference in its entirety.

One unexpected feature of the H5N3 avian viral vaccine construct described herein is that when formulated into a composition comprising a suitable adjuvant, it provides a sterilizing effect when a vaccinated subject is challenged by a pathogenic influenza virus thereby preventing the pathogenic virus from growing in susceptible tissues and being shed into the subject's environment. This surprising feature of the present invention is particularly advantageous over existing vaccines available in the art because it reduces or eliminates disease transmission via a pathogenic virus that may otherwise be transmitted from an immunized subject to a non-immunized, susceptible subject.

Thus, in one aspect, the present invention is directed to vaccine compositions that are effective in preventing and/or ameliorating avian influenza and that, additionally, are capable of preventing the growth, shedding, and transmission of a pathogenic challenge influenza virus from an infected subject to an uninfected subject, such as, for example, from an infected bird to an uninfected bird. More particularly, this invention is directed to a vaccine composition comprising a reverse genetics virus, said reverse genetics virus comprising: (i) an HA portion derived from a first highly pathogenic H5 avian influenza strain, (ii) an N portion derived from a second low pathogenic strain of avian influenza that has an N subtype distinct from the N subtype of the first highly pathogenic H5 avian influenza strain, and (iii) a backbone avian influenza viral genome from a third low pathogenic virus.

Within certain embodiments, the second low pathogenic strain and the third low pathogenic strain are from the same avian influenza virus isolates. Within alternative embodiments, the second low pathogenic strain and the third low pathogenic strain are from distinct avian influenza virus isolates.

Further aspects of the present invention provide avian influenza vaccine compositions and formulations that are effective in preventing or ameliorating an avian influenza virus infection. Such inventive formulation comprises a reverse genetics strain of an avian influenza virus, typically an inactivated form of a reverse genetics strain of an avian influenza virus and, optionally, one or more surfactant comprising a sorbitan oleate esters. Typically, the avian influenza virus vaccine comprises a hemagglutinin (HA) total that is at least about 75 HA/dose of the vaccine formulation.

A vaccine composition that is effective in preventing or ameliorating Avian influenza virus infection, which comprises reverse genetics virus consisting of an HA portion derived from a highly pathogenic strain of H5 avian influenza, a N portion derived from a second low pathogenic strain which has an N subtype different from that of the virus from which the HA portion is derived, and the remaining viral genome selected from a low pathogenic virus which may be the same or different than the virus from which the N portion is derived, adjuvanted with a biologically acceptable adjuvant material, wherein the hemagglutinin (HA) total is at least about 75 HA/dose, or at least about 125 HA/dose, or about 250 HA/dose of said vaccine composition.

Within certain aspects, vaccine compositions and/or formulations may, optionally, further comprise one or more surfactants such as, for example, one or more sorbitan oleate ester and/or one or more ethylene oxide/propylene oxide block copolymer(s). Within certain such embodiments, the sorbitan oleate esters are TWEEN® 80 and/or sorbitan sesquioleate ester. Within other aspects, vaccine compositions and/or formulations may comprise an inventive avian influenza virus that is adjuvanted in a water-in-oil emulsion.

Exemplified herein are vaccine compositions wherein the backbone viral genome is derived from the H1N1 avian influenza virus designated A/Puerto Rico/8/34 (aka PR8). This low pathogenic strain is particularly advantageous in applications requiring an influenza vaccine that is safe across two or more different species.

The present invention further provides vaccine compositions comprising at least two strains of avian influenza wherein the HA/dose is typically greater than about 75

HA/dose, more typically greater than about 128 HA/dose, or greater than about 200 HA/dose, or greater than about 250-300 HA/dose.

It will be understood that the particular avian influenza strains selected to derive the reverse genetics influenza virus vaccine of the present invention dependent upon the particular strain prevalent in the given geographical region in which the vaccine is to be administered with the provisos that (a) the HA subtype is typically the same as the HA subtype of the prevalent or challenge strain and (b) the NA subtype is distinct from the NA subtype of the prevalent or challenge strain so as to enable reliance upon the DIVA technology.

Other aspects of the present invention provide methods for preventing or ameliorating an outbreak of an avian influenza virus infection, which methods comprise the step of administering to a poultry member a vaccine a composition comprising an inactivated reverse genetics avian influenza virus, wherein the hemagglutinin (HA) total is at least about 75 HA/dose of the vaccine composition.

For example, the present invention provides methods for preventing or ameliorating an outbreak of Avian Influenza virus infection, which methods comprise the step of administering to a poultry member a virus or vaccine composition as disclosed herein. The virus or vaccine composition may, for example, be administered via drinking water or via spraying. Typically, the suitable dose is within the range of between about 1 ng and about 1 µg, or between about 5 ng and about 250 ng, or between about 20 ng and about 125 ng, or between about 50 ng and about 100 ng. Effective doses may, generally, be administered at about 0.25 mL to 2.0 mL per poultry member. The virus and/or vaccine may be administered as a single dose, or may be administered repeatedly in two or more doses.

These and other embodiments, features and advantages of the invention will become apparent from the detailed description and the appended claims set forth herein below.

BRIEF DESCRIPTION OF THE DRAWINGS AND SEQUENCE IDENTIFIERS

FIG. 1 is an alignment of goose HK 437H5 and chicken VN C58H5.

SEQ ID NO: 1 is the amino acid sequence of goose HK 437H5 (dqicigyhannstepqvdtimekn-vtvthaqdilekthngklcdldgvkp-lilrdcsvagwllgnpmcdefinvpewsyivekaspan dlcypgdfnnyeel-khllsrtnhfekiqiipksswsnhdass-gvssacpyhgkssffrnvvwlikknsayptikrsynntnqedllvlw gihhp-ndaaeqtklyqnpttyisvgtstlnqr-lvpeiatrpkvngqsgrmeffwtilkpndainfesngnfiapeyaykivkkgd saim kseleygncntkcqtpmgainssmpfh-nihpltigecpkyvksnrlvlatglrn-tpqietrglfgaiagfieggwqgmvdgwygyhh sneqgsgyaadkestq-kaidgvtnkvnsiidkmntqfeavgrefnnlerrienlnkkmedgfldvwtyna ellvlmenertldfhdsn aknlydkvrlqlrdnakelgngcfefyh-kcdnecmesvkngtydypqyseearln-reeisgvklesmgtyqilsiystvasslalaimv aglslwmcsngslqcrici).

SEQ ID NO: 2 is the amino acid sequence of chicken VN C58H5 (DQICIGYHANNSTEQVDTIMEKN-VTVTHAQDILEKTHNGKLCDLDGVKPLILRDCSVAG WLLGNPMCDEFINVPEWSYIVEKAN-PVNDLCYPGDFNDYEELKHLLSRINHFEKIQIIPKS SWSSHEASLGVSSACPYQGKSSFFRNV-VWLIKKNSTYPTIKRSYNNTNQEDLLVLWGIH HPNDAAEQTKLYQNPTTYISVGTSTLN-QRLVPRIATRSKVNGQSGRMEFFWTILRPNDAI NFESNGNFIAPEYAYKIVKKGDSTIMK-SELEYGNCNAKCQTPMGAINSSMPFHNIHPLTI GECP-KYVKSNRLVLATGLRNSPQIETRGLFGA-IAGFIEGGWQGMVDGWYGYHHSNEQG SGYAADKESTQKAIDGVTNKVNSIIDK-MNTQFEAVGREFNNLERRIENLNKKMEDGFLD VWTYNAELLVLMENERTLDFHDSNVKN-LYDKVRLQLRDNAKELGNGCFEFYHKCDNE CMES-VRNGTYDYPQYSEEARLKREEIS-GVKLESIGIYQILSIYSTVASSLVLAIMVAGLSL WMCSNGSLQCRICI).

DETAILED DESCRIPTION OF THE INVENTION

The present invention is based upon the unexpected discovery that reverse genetics technology may be suitably employed to generate low pathogenicity avian influenza viruses from highly pathogenic virus while maintaining the protective capacity derived from a high pathogenicity virus. The monovalent low pathogenicity avian influenza virus vaccines disclosed herein are provide effective protection, with no evidence of shedding of the challenge virus.

The present invention will be best understood by reference to the following definitions:

Definitions

The term "influenza virus" is used herein to define a viral species of which pathogenic strains cause the disease known as influenza or flu.

The term "master strain virus" refers to a viral strain that provide a backbone that is used in the construction of a low pathogenicity influenza virus vaccine strain by the reverse genetics approach as described herein. These master strains typically contribute six or seven gene segments to the vaccine virus (PB1, PB2, PA, NP, M, NS, and, optionally, NA). That is, the master strain virus may optionally be used to as a source for the NA gene. In the specific case of the H5N3 avian influenza viral vaccine described herein, the "master strain virus" contributing the backbone genes is the H1N1 avian viral isolate designated A/Peurto Rico/8/34.

The term "polypeptide" refers to a polymer of amino acids and does not refer to a specific length of the product; thus, peptides, oligopeptides, and proteins are included within the definition of polypeptide. This term also does not refer to, or exclude, post-translational modifications of the polypeptide, for example, glycosylations, acetylations, phosphorylations, and the like.

As used herein, "infectious" refers to the ability of a virus to replicate in a cell and produce viral particles. Infectivity can be evaluated either by detecting virus, i.e., viral load, or by observing disease progression in the animal.

An "individual" or "subject" or "animal", as used herein, refers to vertebrates that support a negative strand RNA virus infection, specifically influenza virus infection, including, but not limited to, birds (such as water fowl and chickens) and members of the mammalian species, such as canine, feline, lupine, mustela, rodent (racine, and murine, etc.), equine, bovine, ovine, caprine, porcine species, and primates, the latter including humans.

As used herein, the term "immunogenic" means that the virus or polypeptide is capable of eliciting a humoral or cellular immune response, and preferably both. An immunogenic entity is also antigenic. An immunogenic composition is a composition that elicits a humoral or cellular immune response, or both, when administered to an animal.

A molecule is "antigenic" when it is capable of specifically interacting with an antigen recognition molecule of the immune system, such as an immunoglobulin (antibody) or T cell antigen receptor. An antigenic polypeptide contains an "epitope" of at least about five, and preferably at least about 10, amino acids. An antigenic portion of a polypeptide, also called herein the "epitope", can be that portion that is immunodominant for antibody or T cell receptor recognition, or it can be a portion used to generate an antibody to the molecule by conjugating the antigenic portion to a carrier polypeptide for immunization. A molecule that is antigenic need not be itself immunogenic, i.e., capable of eliciting an immune response without a carrier.

As used herein, the term "amino acid substitution" refers to the presence of an amino acid at a particular location in the amino acid sequence of that molecule. The amino acid substitution occurs relative to any other amino acid that could have occupied that location. The polypeptide that results from the amino acid sequence change may include changes in post-translational modifications such as glycosylations, acetylations, phosphorylations or any other amino acid modifications as well as the amino acid substitution.

The term "reverse genetics system" as used herein refers to methods of generating influenza virus particles, polypeptides, virons or nucleic acids by genetic engineering methods. These methods include but are not limited to the "plasmid system" as described by Hoffmann (Hoffmann et al., *Vaccine* 20:3165 (2002); U.S. Patent Publication No. 2002/0164770A1, filed Nov. 7, 2002, which is hereby incorporated by reference in its entirety. Generally, reverse genetics systems allow for the creation of virus particles, polypeptides, and/or nucleic acids with specific sequences by genetic engineering methods known to those of skill in the art. These systems are also described in greater detail below.

As used herein the term "receptor binding site" refers to the portion of the HA molecule where the receptor of interest, such as sialic acid receptor on a red blood cell, binds. The structures of the H5 molecules of goose HK 437H5 and chicken VN C58H5 are disclosed herein as SEQ ID NOs; 1 and 2 and are shown in alignment for display of sequence divergence in FIG. 1. The structure of the H5 molecule of A/duck/Singapore, and the location of the receptor binding site for hemagglutinin of this H5 subtype, is described I Ha et al., *Proc. Natl. Acad. Sci. U.S.A.* 98:11181 (2001).

The term "diagnostic reference virus" refers to a virus with enhanced HA antigenicity. Such a diagnostic reference virus can be used in an immunoassay, e.g., the hemagglutinin inhibition assay.

The term "exposure virus" refers to a virus to which an individual animal has been exposed. This exposure can be in the course of daily activities, such as contact with an infected subject, e.g., leading to exposure of a human to an infectious influenza virus. The exposure can also be due to a specific clinical challenge, such as in a laboratory testing situation where a laboratory animal is intentionally exposed to a virus. Such exposure can be expressly generated through immunization with an influenza vaccine.

The phrase "pharmaceutically acceptable" refers to molecular entities and compositions that are physiologically tolerable and do not typically produce an allergic or similar untoward reaction, such as gastric upset, dizziness and the like, when administered to a human. Preferably, as used herein, the term "pharmaceutically acceptable" means approved by a regulatory agency of the Federal or a state government or listed in the U.S. Pharmacopeia or other generally recognized pharmacopeia for use in animals, and more particularly in humans.

The term "carrier" refers to a diluent, adjuvant, excipient, or vehicle with which the compound is administered. Such pharmaceutical carriers can be sterile liquids, such as water and oils, including those of petroleum, animal, vegetable or synthetic origin, such as peanut oil, soybean oil, mineral oil, sesame oil and the like. Water or aqueous solution saline solutions and aqueous dextrose and glycerol solutions are preferably employed as carriers, particularly for injectable solutions. Suitable pharmaceutical carriers are described in "Remington's Pharmaceutical Sciences" by E. W. Martin, 18$^{th}$ Edition.

As used herein, the term "adjuvant" refers to a compound or mixture that enhances the immune response to an antigen. An adjuvant can serve as a tissue depot that slowly releases the antigen and also as a lymphoid system activator that non-specifically enhances the immune response (Hood, et al., *Immunology, Second Ed.*, Menlo Park, Calif.: Benjamin/Cummings, 1984. p. 384). Often, a primary challenge with an antigen alone, in the absence of an adjuvant, will fail to elicit a humoral or cellular immune response. Adjuvants include, but are not limited to, complete Freund's adjuvant, incomplete Freund's adjuvant, saponin, mineral gels such as aluminum hydroxide, surface active substances such as lysolecithin, pluronic polyols, polyanions, peptides, oil or hydrocarbon emulsions, keyhole limpet hemocyanins, and potentially useful human adjuvants such as N-acetyl-muramyl-L-threonyl-D-isoglutamine (thr-MDP), N-acetyl-nor-muramyl-L-alanyl-D-isoglutamine, N-acetylmuramyl-L-alanyl-D-isoglutaminyl-L-alanine-2-(1'-2'-dipalmitoyl-sn-glycero-3-hydroxyphosphoryloxy)-ethylamine, BCG (bacille Calmette-Guerin) and *Corynebacterium parvum*. Preferably, the adjuvant is pharmaceutically acceptable.

As used herein, the term "isolated" means that the referenced material is removed from its native environment, e.g., a cell or virus. Thus, an isolated biological material can be free of some or all cellular components, i.e., components of the cells in which the native material occurs naturally (e.g., cytoplasmic or membrane component). A material shall be deemed isolated if it is present in a cell extract or supernatant. In the case of nucleic acid molecules, an isolated nucleic acid includes a PCR product, an isolated mRNA, a cDNA, or a restriction fragment. In another embodiment, an isolated nucleic acid is preferably excised from the chromosome in which it may be found, and more preferably is no longer joined or proximal to non-coding regions (but may be joined to its native regulatory regions or portions thereof), or to other genes, located upstream or downstream of the gene contained by the isolated nucleic acid molecule when found in the chromosome. In yet another embodiment, the isolated nucleic acid lacks one or more introns. Isolated nucleic acid molecules include sequences inserted into plasmids, cosmids, artificial chromosomes, and the like, i.e., when it forms part of a chimeric recombinant nucleic acid construct. Thus, in a specific embodiment, a recombinant nucleic acid is an isolated nucleic acid. An isolated protein may be associated with other proteins or nucleic acids, or both, with which it associates in the cell, or with cellular membranes if it is a membrane-associated protein. An isolated organelle, cell, or tissue is removed from the anatomical site in which it is found in an organism. An isolated material may be, but need not be, purified.

The term "purified" as used herein refers to material that has been isolated under conditions that reduce or eliminate the presence of unrelated materials, i.e., contaminants, including native materials from which the material is obtained. For example, a purified virion is preferably substantially free of host cell or culture components, including tissue culture or egg proteins, non-specific pathogens, and the like. As used herein, the term "substantially free" is used operationally, in the context of analytical testing of the material. Preferably, purified material substantially free of contaminants is at least 50% pure; more preferably, at least 90% pure, and more preferably still at least 99% pure. Purity can be evaluated by chromatography, gel electrophoresis, immunoassay, composition analysis, biological assay, and other methods known in the art.

Methods for purification are well-known in the art. Viral particles can be purified by ultrafiltration or ultracentrifugation, preferably continuous centrifugation (see Furminger, supra). Other purification methods are possible and contemplated herein. A purified material may contain less than about 50%, preferably less than about 75%, and most preferably less than about 90%, of the cellular components, media, proteins, or other nondesirable components or impurities (as context requires), with which it was originally associated. The term "substantially pure" indicates the highest degree of purity which can be achieved using conventional purification techniques known in the art.

In a specific embodiment, the term "about" or "approximately" means within a statistically meaningful range of a value. Such a range can be within an order of magnitude, preferably within 50%, more preferably within 20%, more preferably still within 10%, and even more preferably within 5% of a given value or range. The allowable variation encompassed by the term "about" or "approximately" depends on the particular system under study, and can be readily appreciated by one of ordinary skill in the art.

Reverse Genetics Methodologies

As indicated above, the present invention is based upon the generation of avian influenza viruses and vaccines thereof that are generated by employing reverse genetics methodologies as described in greater detail by working examples presented herein below. In brief, a low pathogenicity reassortant avian influenza virus is constructed by combining an HA gene from a first high pathogenicity avian influenza virus and an NA gene from a second low pathogenicity avian influenza virus into a backbone from a second or third low pathogenicity avian influenza virus, which comprises the remaining avian influenza viral genes. As indicated above, the exemplary low pathogenicity reassortant avian influenza virus disclosed and exemplified herein was constructed by combining an HA gene from the A/Ck/Vietnam/C58/04 isolate (H5N1) and an NA gene from the A/DK/Germany/1215/73 isolate (H2N3) into the A/Puerto Rico/8/34 backbone to generate an H5N3 virus.

Recently developed reverse-genetics systems have allowed the manipulation of the influenza viral genome (Palese et al., Proc. Natl. Acad. Sci. U.S.A. 93:1354 (1996); Neumann and Kawaoka, Adv. Virus Res. 53:265 (1999); Neumann et al., Proc. Natl. Acad. Sci. U.S.A. 96:9345 (1999); Fodor et al., J. Virol. 73:9679 (1999); US Patent Application 20040029251). For example, it has been demonstrated that the plasmid-driven expression of eight influenza vRNAs from a pol I promoter and all mRNAs from a polII promoter result in the formation of infectious influenza A virus (Hoffmann et al., Proc. Natl. Acad. Sci. USA 2000, 97:6108; US Patent Publication No. 20020164770, which is incorporated by reference for its description of a minimal plasmid reverse genetics system, and for its description of genetic engineering methods).

These recombinant methods allow for the specific production of influenza virus types with specific alterations to the polypeptide amino acid sequence. A HA molecule containing a desired substitution may be part of a recombinant influenza virus. The recombinant influenza virus may be made by any means known to those of skill in the art, including through a genetic engineering method such as the "plasmid only" system (Hoffmann et al., Vaccine 2002, 20:3165). The recombinant influenza virus may be derived from a H5N1 virus. The recombinant virus may have the genetic background of a H1N1 virus used in vaccine development such as A/PR/8/34 virus or any influenza A virus, including cold-adapted strains of A/Leningrad/134/17/57, A/Leningrad/134/47/57 and A/AnnArbor/6/60. The nucleic acid corresponding to the HA molecule sequence may be isolated from the virus and sequenced.

Techniques to isolate and modify specific nucleic acids and proteins are well known to those of skill in the art. In accordance with the present invention there may be employed conventional molecular biology, microbiology, and recombinant DNA techniques within the skill of the art. Such techniques are explained fully in the literature. See, e.g., Sambrook, Fritsch & Maniatis, *Molecular Cloning: A Laboratory Manual*, Second Edition. Cold Spring Harbor, N.Y.: Cold Spring Harbor Laboratory Press, 1989 (herein "Sambrook et al., 1989"); *DNA Cloning. A Practical Approach*, Volumes I and II (D. N. Glover ed. 1985); *Oligonucleotide Synthesis* (M. J. Gait ed. 1984); *Nucleic Acid Hybridization* [B. D. Hames & S. J. Higgins eds. (1985)]; *Transcription And Translation* [B. D. Hames & S. J. Higgins, eds. (1984)]; *Animal Cell Culture* [R. I. Freshney, ed. (1986)]; *Immobilized Cells And Enzymes* [IRL Press, (1986)]; B. Perbal, A *Practical Guide To Molecular Cloning* (1984); Ausubel, F. M. et al. (eds.). *Current Protocols in Molecular Biology*. John Wiley & Sons, Inc., 1994. These techniques include site directed mutagenesis employing oligonucleotides with altered nucleotides for generating PCR products with mutations (e.g., the "Quikchange" kit manufactured by Stratagene).

Low Pathogenicity Avian Influenza Virus Vaccines

The present low pathogenicity avian influenza virus vaccines are exemplified herein by a reassortant H5N3 virus generated by combining the H5 gene from the highly pathogenic Asian outbreak strain A/Ck/Vietnam/C58/04 (H5N1), the N3 gene from the low pathogenic avian influenza strain A/DK/Germany/1215/73 (H2N3), into the low pathogenic avian influenza virus backbone A/Puerto Rico/8/34 (H1N1; PR8). Low pathogenicity avian influenza viruses of the present invention ensure optimum protection against otherwise highly pathogenic avian influenza viruses. Replacement of the N1 gene from A/Puerto Rico/8/34 with the N3 gene from A/DK/Germany/1215/73 facilitates the use of a DIVA program for determining whether anti-neuraminidase antibody titres within individual birds are the result of highly pathogenic viral infection versus low pathogenicity viral vaccination.

The avian influenza isolates useful for the derivation of the vaccines of the present invention may be isolated using techniques available in the art. For example, tissue or serum from infected chickens may be obtained from a commercial broiler flock. The virus may then be passaged in tissue or other suitable media to establish a master seed virus. Further characterization by the skilled artisan may also be undertaken using available methods. The viruses may be inactivated using available methods, such as heat and chemical treatment, for example.

Formulations Comprising Low Pathogenicity Avian Influenza Virus Vaccine(s)

Also provided herein are vaccine formulations comprising one or more low pathogenicity avian influenza virus vaccine of the present invention in combination with an adjuvant and/or emulsion preparation. Such formulations disclosed herein exhibit improved efficacy with reduced concentrations of HA units as compared to concentrations of HA units previously described. More specifically, low pathogenicity avian influenza virus vaccines are effective in the inventive formulations at HA units between about 10 ng and about 1 µg, more typically between about 20 ng and about 500 ng, still more typically between about 50 ng and about 250 ng, or between about 75 ng and about 200 ng, most typically about 100 ng, about 125 ng, about 150 ng, or about 175 ng.

The vaccine composition of the invention may be formulated using available techniques, preferably with a pharmacologically acceptable carrier. For example, in one embodiment an aqueous formulation is contemplated. Such formulations utilize water, saline, or phosphate or other suitable buffers. In still another embodiment, the vaccine composition is preferably a water-in-oil or oil-in-water emulsion. Also contemplated are double emulsions, often characterized as water-in-oil-in-water emulsions. The oil may help to stabilize the formulation and further function as an adjuvant or enhancer. Suitable oils include, without limitation, white oil, Drakeoil, squalane or squalene, as well as other animal, vegetable or mineral oils, whether naturally-derived or synthetic in origin.

As exemplified below, a modified virus containing an increased antigenicity HA molecule itself is more immunogenic, which in turn provides for a stronger immune response and better vaccine potential.

Strategies to enhance influenza vaccine effectiveness include the use of adjuvants (Wood and Williams, supra), co-administration of immunostimulatory molecules (Salgaller and Lodge, J. Surg. Oncol. 1998, 68:122) and mucosal vaccination strategies. Mucosal immunization strategies include encapsulating the virus in microcapsules (U.S. Pat. No. 5,075,109, No. 5,820,883, and No. 5,853,763) and using an immunopotentiating membranous carrier (WO 98/0558). In addition, the immunogenicity of orally administered immunogens can be enhanced by using red blood cells (rbc) or rbc ghosts (U.S. Pat. No. 5,643,577), or by using blue tongue antigen (U.S. Pat. No. 5,690,938). Although these approaches are promising for improved future vaccination strategies, their use in specific situations requires validation and surveillance to ensure vaccine effectiveness. It is contemplated that the invention described herein will enhance these strategies including by increasing the ability to detect their immunogenic effects.

In addition, the vaccine composition may contain other suitable adjuvants available in the art. These can include aluminum hydroxide and aluminum phosphate, for example, as well as other metal salts.

Additional excipients may also be included in the vaccine composition, such as surfactants or other wetting agents or formulation aids. Surfactants can include the sorbitan monooleate esters (TWEEN® series), as well as the ethylene oxide/propylene oxide block copolymers (PLURONIC® series), as well as others available in the art. Other compounds recognized as stabilizers or preservatives may also be included in the vaccine. These compounds include, without limitation, carbohydrates such as sorbitol, mannitol, starch, sucrose, dextrin or glucose and the like, as well the preservative formalin, for example.

The vaccine composition may also be formulated as a dry powder, substantially free of exogenous water, which may then be reconstituted by an end user prior to administration. The vaccine composition may, optionally, be formulated utilizing killed or inactivated virus.

The vaccine composition of the invention will preferably contain a minimum of about 200 HA total from its influenza viral components. In one embodiment of the invention, the vaccine will contain about 128 HA/dose from each strain, and even more preferably about 192 HA/dose from each strain.

Other poultry antigens against other diseases may also be included and administered with the vaccine composition of the invention. For example, vaccine antigens against chicken herpes virus, chicken anemia virus (CAV), Newcastle Disease virus and Infectious Bronchitis (IB) virus, as well as reovirus antigens may be included as part of the vaccine composition of the invention. One or more reovirus antigens may be particularly preferred as part of the vaccine composition of the invention.

Methods for Inducing a Protective Immune Response

The present invention also provides methods for inducing protection against infection from an avian influenza virus. Methods disclosed herein involve administering to a poultry animal a vaccine and/or formulation thereof comprising at one or more low pathogenicity avian viral vaccine(s) described above wherein the one or more low pathogenicity avian viral vaccine(s) comprise a combined HA content of greater than about 75 HA/dose, more typically greater than about 125 HA/dose, or greater than about 200 HA/dose, or between about 250 HA/dose and about 300 HA/dose.

The mode of administration may be selected by the skilled artisan and will depend upon the precise application contemplated. For instance, vaccine compositions may be administered to post-hatch, young (few days to several weeks old) chicks via drinking water, spraying or eye drops. In ovo administration is contemplated herein. For example, embryos may be inoculated, usually at about day 18-19. Other methods wherein the vaccine composition of the invention is administered parenterally, subcutaneously, peritoneally, orally, intranasally, or by other available means, preferably parenterally, more preferably intramuscularly, in effective amounts according to a schedule which may be determined according to the time of anticipated potential exposure to a carrier of the disease-causing Avian Influenza Virus, are also within the scope of the invention.

A dose is typically within the range of about 0.25 mL to about 2.0 mL per poultry animal, more preferably about 0.5 mL to about 1.0 mL per animal. Thus, one, two or more doses are contemplated herein, with as few as possible being particularly preferred.

As set forth above, the invention is directed to novel avian influenza vaccine compositions and methods for use thereof poultry. The term "poultry" is intended to encompass, without limitation, all commercially-bred poultry animals, including chickens, ducks, geese, turkeys, peafowl, bantam fowl, and the like.

Immunoassays

Various means known in the art for detecting immunospecific binding of an antibody to an antigen can be used to detect the binding and increased antigenicity in accordance with the present invention. An early method of detecting interaction between an antigen and an antibody involved detection and analysis of the complex by precipitation in gels. A further method of detecting an analyte-detector antibody binding pair includes the use of radioiodinated detector antibodies or a radioiodinated protein which is reactive with IgG, such as Protein A. These early methods are well known to persons skilled in the art, as reviewed in Methods in Enzymology 1980, 70:166-198.

Later methods for determining the presence of an analyte in a sample using only one antibody include competitive binding assays. In this technique the antibody, which most often would be immobilized onto a solid support, would be exposed to a sample suspected of containing the analyte together with a known quantity of labeled analyte. The two analytes, the labeled analyte and the analyte in the sample, would then compete for binding sites on the antibody. Either free labeled analyte or bound labeled analyte is determined and from this measurement the amount of competing analyte in the sample is known. A more complete description of this method is disclosed in "Basic Principles of Antigen-Antibody Reaction" (Labat, Methods in Enzymology, 70, 3-70, 1980). In this example the labeled analyte can be labeled with either a radioisotope or an enzyme label.

More current immunoassays utilize a double antibody method for detecting the presence of an analyte. These techniques are also reviewed in the above referenced volume of Methods in Enzymology. Therefore, according to one embodiment of the present invention, the presence of the individual markers is determined using a pair of antibodies for each of the markers to be detected. One of said pairs of antibodies is referred to herein as a "detector antibody" and the other of said pair of antibodies is referred to herein as a "capture antibody". One embodiment of the present invention thus uses the double antibody sandwich method for detecting an analyte in a sample of biological fluid. In this method, the analyte is sandwiched between the detector antibody and the capture antibody, the capture antibody being irreversibly immobilized onto a solid support. The detector antibody would contain a detectable label, in order to identify the presence of the antibody-analyte sandwich and thus the presence of the analyte.

Common early forms of solid supports include plates, tubes or beads of polystyrene, all of which are well known in the field of radioimmunoassay and enzyme immunoassay. More recently, a number of porous materials such as nylon, nitrocellulose, cellulose acetate, glass fibers, and other porous polymers have been employed as solid supports.

Various techniques and corresponding sensor devices may be used. Automated assay apparatuses include continuous/random access assay apparatus. Examples of such systems include OPUS™ of PB Diagnostic System, Inc. and the IMX™ Analyzer introduced by Abbott Laboratories of North Chicago, Ill. The automated assay instruments of PB Diagnostic Systems, Inc. are described in U.S. Pat. Nos. 5,051,237; 5,138,868; 5,141,871 and 5,147,609.

Further classes of immunochemical analyzer systems, which can be used in practicing the present invention, are optical immunosensor systems. In general an optical immunosensor is a device that uses optical principles quantitatively to convert chemical or biochemical concentrations or activities of interest into electrical signals. These systems can be grouped into four major categories: reflection techniques; surface plasmon resonance; fiber optic techniques and integrated optic devices. Reflection techniques include ellipsometry, multiple integral reflection spectroscopy, and fluorescent capillary fill devices. Fiber-optic techniques include evanescent field fluorescence, optical fiber capillary tube, and fiber optic fluorescence sensors. Integrated optic devices include planer evanescent field fluorescence, input grading coupler immunosensor, Mach-Zehnder interferometer, Hartman interferometer and difference interferometer sensors. Holographic detection of binding reactions is accomplished detecting the presence of a holographic image that is generated at a predetermined image location when one reactant of a binding pair binds to an immobilized second reactant of the binding pair (see U.S. Pat. No. 5,352,582, issued Oct. 4, 1994 to Lichtenwalter et al.). Examples of optical immunosensors are described in general in a review article by G. A. Robins, Advances in Biosensors 1991, 1:229-256. More specific descriptions of these devices are found for example in U.S. Pat. Nos. 4,810,658; 4,978,503; and 5,186,897; R. A. Brady et al. (Phil. Trans. R. Soc. Land. B. 1987, 316:143-160) and G. A. Robinson et al. (in Sensors and Actuators, Elsevier 1992).

Serological assays are widely used in the determination of influenza diagnosis as well as in research studies regarding the epidemiology and antigenicity of viral strains. In particular, the hemagglutinin inhibition (HI) assay is widely used due to its minimal laboratory requirements and ease of use. It is contemplated that the invention will improve the applicability of the HI assay by increasing its sensitivity. The HI assay may also be used to show the antigenicity of the modified HA molecule, and assist in the characterization of the modified HA molecule as more or less antigenic than non-modified molecules.

The HI assay determines the ability of antibodies from a serum sample to bind with a standardized reference. In the HI assay, serial dilutions (titers) of serum sample are mixed with standard amounts of erythrocytes and their association into complexes is detected visually. The lowest level of titered serum that results in a visible complex is the assay result.

As noted above, the present invention provides for improved production and validation of vaccines for treating or preventing influenza viral infections. In particular, the instant invention is applicable to vaccines made using reverse genetic techniques. It is contemplated that the invention will be of use in the validation and verification of the immune response after vaccination. In particular, but not exclusively, the invention provides for the enhanced detection of antibodies after an individual has been exposed to an influenza virus because of the enhance antigenicity of the modified HA molecule. This enhanced antigenicity is reflected in the increased sensitivity of the assay used to detect the immune response, such as the HI assay.

EXAMPLES

The present invention will be better understood by reference to the following examples, which illustrate the invention without limiting it.

Example 1

Construction of H5N3 Avian Influenza Vaccine

Viruses

Influenza viruses A/PR/8/34 (H1N1), A/Chicken/Vietnam/C58/04 (H5N1), and A/DK/Germany/1215/73 (H2N3) may be obtained from the repository of St. Jude Children's Research Hospital. A/Muscovy Duck/Vietnam/453/2004H5N1 may be obtained from the Regional Animal Health Centre, Ho Chi Minh City, Vietnam.

RT-PCR and Construction of Plasmids

RNA is isolated from the A/Chicken/Vietnam/c58/04 (H5N1), A/PR/8/34 (H1N1), and A/DK, Germany/1215/73 (H2N3) influenza viruses using the RNeasy kit (Qiagen). RNA is reverse-transcribed to cDNA by using the Uni 12-primer (AGC AAA AGC AGG; SEQ ID NO: 3).

The resulting cDNA is then amplified using segment-specific primers described in Hoffmann et al. (2001) Arch. Virol. 146: 2275-2289, which is herein incorporated by reference. In particular, the segment-specific primers may be used as described in Table 1:

TABLE 1

| Primers that may be Used to Amplify Influenza Viral Segments | | |
|---|---|---|
| Gene | Forward Primer | Reverse Primer |
| PB2 | Ba-PB2-1: TATTGGTCTCAGGGAGCGAAAGC AGGTC SEQ ID NO: 4 | Ba-PB2-2341R: ATATGGTCTCGTATTAGTAGAAAC AAGGTCGTTT SEQ ID NO: 5 |
| PB1 | Bm-PB1-1: TATTCGTCTCAGGGAGCGAAAGCA GGCA SEQ ID NO: 6 | Bm-PB1-2341R: ATATCGTCTCGTATTAGTAGAAAC AAGGCATTT SEQ ID NO: 7 |
| PA | Bm-PA-1: TATTCGTCTCAGGGAGCGAAAGCA GGTAC SEQ ID NO: 8 | Bm-PA-2233R: ATATCGTCTCGTATTAGTAGAAAC AAGGTACTT SEQ ID NO: 9 |
| HA | Bm-HA-1: TATTCGTCTCAGGGAGCAAAAGCA GGGG SEQ ID NO: 10 | Bm-NS-890R: ATATCGTCTCGTATTAGTAGAAAC AAGGGTGTTTT SEQ ID NO: 11 |
| modified-HA (1) | Bm-HA-1: TATTCGTCTCAGGGAGCAAAAGCA GGGG SEQ ID NO: 10 | Bm-H5-1025R: ATTACGTCTCTCCTCTTGTCTCAAT TTGAGGGGTATT SEQ ID NO: 12 |
| modified-HA (2) | Bm-H5-1020: ATTACGTCTCAGAGGACTATTTGG GGCTATAGCAGG SEQ ID NO: 13 | Bm-NS-890R: ATATCGTCTCGTATTAGTAGAAAC AAGGGTGTTTT SEQ ID NO: 11 |
| NP | Bm-NP-1: TATTCGTCTCAGGGAGCAAAAGCA GGGTA SEQ ID NO: 14 | Bm-NP-1565R: ATATCGTCTCGTATTAGTAGAAAC AAGGGTATTTTT SEQ ID NO: 15 |
| NA | Ba-NA-1: TATTGGTCTCAGGGAGCAAAAGC AGGAGT SEQ ID NO: 16 | Ba-NA-1413R: ATATGGTCTCGTATTAGTAGAAAC AAGGAGTTTTTT SEQ ID NO: 17 |
| M | Bm-M-1: TATTCGTCTCAGGGAGCAAAAGCA GGTAG SEQ ID NO: 18 | Bm-M-1027R: ATATCGTCTCGTATTAGTAGAAAC AAGGTAGTTTTT SEQ ID NO: 19 |
| NS | Bm-NS-1: TATTCGTCTCAGGGAGCAAAAGCA GGGTG SEQ ID NO: 20 | Bm-NS-890R: ATATCGTCTCGTATTAGTAGAAAC AAGGGTGTTTT SEQ ID NO: 21 |

The 5' end of the primers has recognition sequences for the restriction endonucleases BsmBI (Bm) or BsaI (Ba).

Plasmids encoding the PB1, PB2, PA, NP, M and NS genes of influenza A/PR/8/34 may be constructed as described in Hoffmann et al. (2002) Vaccine 20: 3165-3170, which is herein incorporated by reference. In particular, the PB2, PB1, PA, NP, M and NS influenza genes may be amplified from A/PR/8/34 (H1N1) cDNA using the primers listed in Table 1. The PB1, PB2, PA, NP, M and NS genes are cloned by digesting the PCR fragments with either BsmBI (PB1, PA, NP, M and NS) or BsaI (PB2) and ligating them into the cloning vector pHW2000 (also cut with either BsmBI or BsaI). These plasmids are designated pHW191-PB2, pHW192-PB1, pHW193-PA, pHW195-NP, pHW197-M and PHW198-NS.

The NA gene is amplified from A/DK/Germany/1215/73 (H2N3) cDNA. The NA gene is amplified by PCR using the NA specific primers described in Table 1 (SEQ ID NO: 16 and SEQ ID NO: 17). The PCR fragment is digested with BsaI and ligated into the vector pHW2000.

The HA gene is amplified from A/Chicken/Vietnam/c58/04 (H5N1) cDNA by PCR using the HA specific primers described in Table 1 (SEQ ID NO: 10 and SEQ ID NO: 11). The PCR fragment is digested with BsmBI and ligated into the vector pHW2000. The HA gene from A/Chicken/Vietnam/C58/04 (H5N1) is then modified by deletion of a polybasic amino acid region at the cleavage site between HA1 and HA2. A plasmid containing the modified HA gene is derived by PCR amplification of two fragments of the plasmid encoding the unmodified HA. The primers used for amplification of the two fragments are listed in Table 1 (SEQ ID NO: 10 and SEQ ID NO: 12; SEQ ID NO: 13 and SEQ ID NO: 11). The fragments are digested with BsmBI and ligated into pHW2000-BsmBI by a three-fragment ligation reaction.

To ensure that the genes are free of unwanted mutations, the cloned viral cDNAs are sequenced.

Generation of Recombinant Viruses

Recombinant viruses may be generated by DNA transfection as described in Hoffman et al. (2002) Vaccine 20: 3165-

3170, which is herein incorporated by reference. In particular, 293T and MDCK cells may be co-cultured (0.2 to $1\times10^6$ cells of each cell line) and used for the transfection experiments. The co-cultured cells may be transfected with a DNA-lipid complex containing 1 ug of each plasmid, 18 ul of transit LT1 (Panvera, Wis.) in a final volume of 1 ml of OPTIMEM-I (Gibco, N.Y.). Transfection may be carried out for 6 hours, at which time the DNA-lipid complexes may be removed and replaced with fresh medium. The cells may be incubated for an additional 24 hours, and 0.5 ug/ml of TPCK-treated trypsin (Worthington) may be added. After 72 hours, the supernatant may be taken from the cells, and 100 ul may be injected into 10-day-old embryonated chicken eggs.

Preparation of Vaccines

Viruses may be propagated in the allantoic cavities of 10- to 11-day-old embryonated chicken eggs at 35 degrees Celsius for 48 hours. Allantoic fluid may be harvested, and virus may be inactivated by adding beta-propiolactone (BPL) at a ratio of 1:2000 (vol/vol) and allowing the fluid to remain at room temperature for 4 hours and then remaining at 4 degrees Celsius for 24 hours. Inactivation may be confirmed by the absence of detectable infectivity after two blind passages of the treated allantoic fluid in embryonated eggs.

Virus Concentration by Amicon Ultrafiltration

Inactivated viruses in allantoic fluid may be clarified by centrifugation at 5000 rpm for 15 minutes. The supernatant allantoic fluid may be concentrated to $\frac{1}{10}$ of its original volume by use of an Amicon concentrator ultrafiltration apparatus.

Virus Purification

The concentrated viruses may be purified by ultracentrifugation through a 25 and 70% sucrose cushion and then pelleted at 27,000 rpm at 4 degrees Celsius for one hour. The pellet may be resuspended in STE buffer, sonicated for 2 minutes, and then centrifuged on a 25 to 70% sucrose continuous gradient with a SW28 rotor at 24,000 rpm for 2.5 hours. Virus bands may be removed by syringe, diluted in STE, and then pelleted as described above. The pellets may be resuspended and sonicated in appropriate volumes of STE, and sodium azide may be added at 200 ppm final concentration.

Standardization of Vaccine

The content of hemagglutinin protein in the allantoic fluid, Amicon-concentrated vaccine, and purified vaccine may be standardized by the single radial immunodiffusion technique as described in Wood et al. (1985) Avian Dis. 29: 867-872, which is herein incorporated by reference.

Example 2

Efficacy of Inactivated H5N3 Avian Influenza Vaccine in SPF Chickens

Composition of Vaccine

The efficacy of graded doses of an inactivated avian influenza H5N3 vaccine was tested. The avian influenza H5N3 vaccine was prepared essentially as described in Example 1. Four vaccines were prepared, one of which was a placebo vaccine containing virus-free allantoic fluid. The three remaining vaccines contained inactivated avian influenza viral stock to derive final formulations containing 1.2 ug HA protein (307 HAU) per 0.6 mL volume dose, 0.5 ug HA protein (128 HAU) per 0.5 mL volume dose or 0.25 ug HA protein (64 HAU) per 0.5 mL volume dose of antigen as measured by a radial immunodiffusion (or hemagglutination inhibition) assay of the virus stock formulated. The associated dose levels of the vaccines in terms of hemagglutinating units (HAU) were 64, 128 and 307 HAU/dose respectively. Inactivated antigen stock was prepared by one passage in Vero cells during construction of the reassortant virus, followed by six SPF egg passages.

Vaccines were formulated into a water-in-oil emulsion (60:40 oil:aqueous ratio) with mineral oil as the carrier and Tween 80 and Arlacel 83 as emulsifiers. The Tween and antigen components were mixed separately from the Drakeol and Arlacel 83, and the aqueous phase was added slowly to the oil phase while stirring to form a pre-emulsion. The pre-emulsion was then mechanically homogenized using a fixed-head Silverson L4R Homogenizer.

Vaccination

The vaccines were administered intramuscularly in the breast to groups of 25 SPF White Leghorn chickens (*Gallus domesticus*; from Charles River/SPAFAS). Table 2 summarizes the vaccination protocol. Groups 1-3 were vaccinated with 0.5 ml of vaccine, while Group 4 was vaccinated with 0.6 ml of vaccine (see Table 2) using a 3 mL sterile disposable syringe fitted to a 20-gauge, ½"-¾" needle. Chickens in Group 5 remained nonvaccinated at two and five weeks of age. An antigen free placebo vaccine was similarly administered intramuscularly to a group of 25 hatchmates and an additional 25 hatchmates were left as nonvaccinated controls. Primary vaccination occurred when the chickens were 2 weeks of age, with a booster vaccination administered in the same manner when the birds were 5 weeks of age.

TABLE 2

Table of Treatments

| Treatment group (N = 25) | Vaccine | Bleeding | Challenge (8 weeks of age) | Virus shedding |
|---|---|---|---|---|
| 1 | Placebo (lot #2073-14) | At 2, 5 and 8 weeks of age | H5N1 subtype | Tracheal and cloacal swabs at 3, 5, 7, 10 and 14 days post-challenge |
| 2 | 0.25 ug/64 HAU (lot #2073-11) | | | |
| 3 | 0.5 ug/128 HAU (lot #2073-12) | | | |
| 4 | 1.2 ug/307 HAU (lot #2073-13) | | | |
| 5 | Nonvaccinated | | | |

Just prior to the initial vaccination and at three weeks after the vaccinations, blood samples were obtained from the chickens for determination of avian influenza antibody titers by hemagglutination inhibition (HI) assay. Pre-bleed serum samples were all negative.

Challenge and Sample Collection

Challenge was conducted when the chickens reached 8 weeks of age. Chickens were administered the challenge virus A/chicken/Vietnam/c58/04 at a dilution of 1:1054 to yield 30 $CLD_{50}$ per chicken when administered by intranasal/intratracheal instillation in a volume of 1.0 mL. All chickens were observed daily for mortality for 14 days post-challenge.

Blood samples were collected from all birds at 2, 5, 8 and 10-11 weeks of age. The blood was placed at 37 degrees C. for 30 minutes, then moved to 4 degrees Celsius overnight and allowed to clot. The serum was aseptically removed into separate sterile tubes for serologic analysis by hemagglutination inhibition assay. Sera samples were stored at −30 degrees Celsius or colder pending analysis.

At 3, 5, 7, 10 and 14 days post challenge, tracheal and cloacal swabs were obtained from living birds for virus re-isolation in SPF eggs. Swabs were placed in tubes containing 1 mL viral transport medium consisting of a 1:1 mix of PBS/Glycerol with $2\times10^6$ Units/L penicillin, $2\times10^6$ units/L polymixin B, 250 mg/L gentamicin, $0.5\times10^6$ units/L nystatin, 60 mg/L ofloxacin HCL and 0.2 gm/L sulfamethoxazole. Swabs were stored frozen at −70 degrees C. or colder pending analysis.

Serology

Results of serologic testing are reported in Table 3.

TABLE 3

Serologic analysis of pre-vaccination, post-primary vaccination and post-booster vaccination sera by hemagglutination inhibition assay.

| Treatment Group | Pre-vaccination | | 21 days post-primary vaccination | | 21 days post-booster vaccination | |
|---|---|---|---|---|---|---|
| | GMT | #pos/#test | GMT | #pos/#test | GMT | #pos/#test |
| 1 | 0 | 0/25 | 0 | 0/25 | 0* | 0/24* |
| 2 | 0 | 0/25 | 254 | 24/25 | 3671 | 25/25 |
| 3 | 0 | 0/25 | 320 | 25/25 | 4101 | 25/25 |
| 4 | 0 | 0/25 | 446 | 25/25 | 4335 | 25/25 |
| 5 | 0 | 0/25 | 0 | 0/25 | 0 | 0/25 |

*Bird #6, Pen 9 removed from consideration due to mis-vaccination.

Serum samples from all birds collected pre-vaccination were free of avian influenza specific antibody detectable by hemagglutination inhibition assay. At 21 days after primary vaccination, the placebo vaccinated control chickens (Group 1) and nonvaccinated chicken (Group 5) remained free of antibody, while the groups vaccinated with the inactivated prototypes (Groups 2-4) responded with geometric mean titer levels of 254, 320 and 446 respectively.

At 21 days after the second vaccination, the nonvaccinated control chickens (Group 5) remained free of detectable antibody to avian influenza. One bird in the placebo vaccinated group (bird #6, Pen 9) was found to have a titer of 1280, while all other placebo vaccinated birds remained seronegative. As the nonvaccinated pen-mate of bird #6 remained seronegative, inadvertant exposure of the pen to avian influenza is ruled out. The only possible explanation for the antibody response in bird #6 is that during the booster vaccination it mistakenly received a dose of inactivated prototype vaccine rather than placebo vaccine. As such, it is most appropriate to remove the bird from further consideration in calculations of the results of serology or challenge.

All birds administered inactivated prototype vaccine responded, with geometric mean titers for those groups of 3671, 4101 and 4335 respectively.

Protection Against Mortality

Mortality data after challenge is summarized in Table 4.

TABLE 4

Mortality after challenge with A/chicken/Vietnam/c58/04

| Treatment Group | # mortalities/# challenged | % mortality/% protection |
|---|---|---|
| 1* | 24/24* | 100/0* |
| 2 | 0/25 | 0/100 |
| 3 | 0/25 | 0/100 |
| 4 | 0/25 | 0/100 |
| 5 | 25/25 | 100/0 |

*Bird #6, Pen 9 removed from consideration due to mis-vaccination

All birds in the nonvaccinated control group died by 3 days post-challenge. All birds except one in the placebo vaccinated group died by 4 days post-challenge. The one bird which survived challenge (wingband #6, Pen 9) was discussed previously, and removing it from consideration, both the nonvaccinated and placebo vaccinated control groups suffered 100% mortality. This satisfied the validity criteria established for the control groups in which at least 90% mortality was required after challenge.

All birds in all three vaccinated groups survived challenge. The prevented fraction was considered to be 100% (95% CI 86,100). This satisfied the criteria of at least 70% vaccine efficacy for a claim of protection against mortality.

Virus Re-Isolation

Virus reisolation data is summarized in Table 5 for trachea swabs and in Table 6 for cloacal swabs.

TABLE 5

Virus reisolation from trachea after challenge with A/chicken/Vietnam/c58/04

| Treatment Group | # virus positive swabs/ # swabs tested at: | | | | |
|---|---|---|---|---|---|
| | 3 dpc | 5 dpc | 7 dpc | 10 dpc | 14 dpc |
| 1* | 1/1 | Not tested - all birds died prior to 5 dpc sampling | | | |
| 2 | 1/25 | 1/25 | 0/25 | 0/25 | 0/25 |
| 3 | 1/25 | 1/25 | 0/25 | 0/25 | 0/25 |
| 4 | 0/25 | 0/25 | 0/25 | 0/25 | 0/25 |
| 5 | Not tested - all birds died prior to 3 dpc sampling | | | | |

*Bird #6, Pen 9 removed from consideration due to mis-vaccination

TABLE 6

Virus reisolation from cloaca after challenge with A/chicken/Vietnam/c58/04

| Treatment Group | # virus positive swabs/ # swabs tested at: | | | | |
|---|---|---|---|---|---|
| | 3 dpc | 5 dpc | 7 dpc | 10 dpc | 14 dpc |
| 1* | 1/1 | Not tested - all birds died prior to 5 dpc sampling | | | |
| 2 | 0/25 | 0/25 | 0/25 | 0/25 | 0/25 |
| 3 | 0/25 | 0/25 | 0/25 | 0/25 | 0/25 |
| 4 | 0/25 | 0/25 | 0/25 | 0/25 | 0/25 |
| 5 | Not tested - all birds died prior to 3 dpc sampling | | | | |

*Bird #6, Pen 9 removed from consideration due to mis-vaccination

All birds in the nonvaccinated control group died before the first sampling date at three days post-challenge, thus no virus reisolation data for this group was possible.

For the placebo vaccinated group, all birds except two died before the first sampling date. Bird #6, Pen 9, as discussed previously, was mistakenly vaccinated with one of the test vaccines such that it was antibody positive at challenge, and it therefore survived challenge. No virus could be reisolated from trachea or cloaca swabs obtained from this bird at any time after challenge. Virus was reisolated from the trachea and cloaca of the other placebo vaccinated bird (#113, Pen 10) at 3 days post-challenge, one day before its demise.

For Group 2, administered vaccine at the lowest antigen level tested in the study (0.25 ug, 64 HAU/dose), virus was reisolated from the trachea of one of the 25 birds tested at days 3 and 5 post-challenge. Thereafter, and for all other birds in Group 2, there was no reisolation from trachea or cloaca swabs through the end of the study.

For Group 3, administered vaccine formulated to contain an intermediate antigen level (0.5 ug, 128 HAU/dose), virus was reisolated from the tracheas of two birds of the 25 tested, at one sampling point each (one bird at 3 days post-challenge, and the other at 5 days post-challenge). All other samplings for these two birds, and all samplings for all other birds in Group 3 were negative for virus reisolation.

For Group 4, administered vaccine formulated to contain the highest antigen level tested in the study (1.2 ug, 307 HAU/dose), no virus was reisolated from the trachea or cloaca of any of the 25 birds tested at any time.

With the almost complete mortality in the nonvaccinated and placebo control groups prior to sampling, and therefore lack of reisolation data for those groups, no statistical inference could be made with respect to reisolation rates.

Vaccine Efficacy

After vaccination of SPF chickens at two weeks and five weeks of age with the tested prototypes, high levels of antibody were measured by hemagglutination inhibition testing, and complete protection against challenge mortality was observed. There was minimal virus reisolation from vaccinated chickens after challenge, and while it cannot be stated there was a significant reduction in reisolation rates compared to controls (because all controls died before reisolation could be assessed in those groups), it is clear that the vaccine may be capable of inducing significant reduction of shedding. For unequivocal proof of same, it will be necessary to modify the challenge protocol such that non-vaccinated or placebo vaccinated chickens do not immediately die after challenge. This may prove difficult as the H5N1 challenge strain is exceedingly pathogenic in chickens.

Three different antigen levels of this whole-virus inactivated vaccine were tested. Results were essentially the same for all three antigen levels, such that a minimum protective dose was not determined in this study. Further work with vaccines formulated to contain less than 0.25 ug (64 HAU)/dose of antigen will be necessary to determine the minimum. At the current time, it can be concluded that two vaccinations with a water-in-oil adjuvanted emulsion, containing the H5N3 reassortant virus at no less than 0.25 ug (64 HAU)/dose, is highly efficacious in preventing mortality induced by the H5N1 Vietnam virulent field isolate, and is also likely to be effective in preventing shed of virulent H5N1.

The vaccines afforded 100% protection against mortality. Challenge virus reisolation from tracheal and cloacal swabs obtained from all living birds at various timepoints after challenge was minimal. It is concluded that two vaccinations with a water-in-oil adjuvanted emulsion, containing the H5N3 reassortant virus at no less than 0.25 ug (64 HAU) per dose, is highly efficacious in preventing mortality induced by the H5N1 Vietnam virulent field isolate, and is also likely to be effective in preventing shed of virulent H5N1.

Example 3

Inactivated H5N3 Avian Influenze Vaccines in SPF Chickens

Five vaccines were prepared essentially as described in Example 1. The vaccines were formulated to contain the virus content per dose as listed in Table 7 (Table of Treatments). Virus concentrations in terms of HAU and $EID_{50}$ measurements were based on pre-inactivation titration of the virus stock. Antigen concentrations as listed for ug H5 protein were based on post-inactivation measurement of the antigen stock using standardized single radial immunodiffusion (SRID). Based on these measurements of the stock antigen, and the percent antigen fluids formulated, the listed antigen quantities per dose were calculated.

Vaccines were formulated as water-in-oil emulsions (60:40 oil:aqueous ratio) with mineral oil as the carrier and Tween 80 and Arlacel 83 as emulsifiers. The Tween and antigen components were mixed separately from the Drakeol and Arlacel 83, and the aqueous phase was added slowly to the oil phase while stirring to form a pre-emulsion. The pre-emulsion was then mechanically homogenized using a fixed-head Silverson L4R Homogenizer.

TABLE 7

Table of Treatments

| Treatment group | Vaccine | # Birds | Bleed |
|---|---|---|---|
| 1 | 64 HAU/$10^{7.0}$ $EID_{50}$/0.09 ug H5 (lot # 2285-26-06JUL05) | 25 | 21 dpv |
| 2 | 128 HAU/$10^{7.3}$ $EID_{50}$/0.18 ug H5 (lot #2285-21-28JUN05) | 25 | 21 dpv |
| 3 | 256 HAU/$10^{7.6}$ $EID_{50}$/0.35 ug H5 (lot #2250-55-09MAR05) | 25 | 21 dpv |
| 4 | 512 HAU/$10^{7.9}$ $EID_{50}$/0.71 ug H5 (lot #2250-56-09MAR05) | 25 | 21 dpv |
| 5 | 1024 HAU/$10^{8.2}$ $EID_{50}$/1.42 ug H5 (lot #2250-57-09MAR05) | 25 | 21 dpv |
| 6 | Nonvaccinated controls | 25 | Same day as vaccinated groups |

Vaccination

For each vaccine, 25 chickens were vaccinated once, subcutaneously, with 0.5 mL total volume. Twenty-five hatchmates were held as non-vaccinated controls. All birds were individually leg-banded and co-mingled in a floor pen until bled and terminated or shipped to the challenge facility. At three weeks post-vaccination, blood samples were collected from all chickens.

Challenge

Twenty chickens per group from groups 1-4 and 6, selected arbitrarily, were challenged with the highly pathogenic avian influenza A/chicken/Vietnam/c58/04 strain (H5N1 type). 30 chicken-lethal-doses (CLD) of the virus was administered to each chicken via intranasal/intratracheal instillation. This virus dose was previously demonstrated to be effective in inducing 100% mortality in nonvaccinated control chickens as described in Example 2.

Chickens were observed for 14 days after challenge administration for mortality. Additionally, at 4 days post challenge, tracheal and cloacal swabs were obtained from all surviving birds for virus reisolation.

Serological Response

The back-titration of the H5N3 antigen stock/dilution used in the HI assay, confirmed the use of 8 HA units of antigen per 50 uL. The homologous H5N3 serum pool established for use as a positive control sample demonstrated HI activity to a dilution of 1:320 or 1:640. PBS control wells failed to demonstrate HI activity and the 25 nonvaccinated control sera failed to demonstrate HI activity at 1:10 dilution. By the criteria listed in SO #309, these results indicated the HI assay and potency test in general were validly performed.

Antibody response for groups vaccinated with the experimental prototype vaccines (and nonvaccinated control group), as measured by the valid HI assay, is summarized in Table 8 and individual bird results are reported in Tables 9-14.

TABLE 8

Summary of serologic response to vaccination with inactivated prototype H5N3 vaccines as measured by hemagglutination inhibition

| Treatment Group | Antigen/dose | # sera ≥ 1:40 | # sera < 1:40 | % sera ≥ 1:40 | GMT all | GMT NR removed* |
|---|---|---|---|---|---|---|
| 1 (2285-26) | 64 HAU $10^{7.0}$ $EID_{50}$ 0.09 ug H5 | 18 | 7 | 72 | 109 | 195 |
| 2 (2285-21) | 128 HAU $10^{7.3}$ $EID_{50}$ 0.18 ug H5 | 19 | 6 | 76 | 174 | 533 |
| 3 (2250-55) | 256 HAU $10^{7.6}$ $EID_{50}$ 0.35 ug H5 | 20 | 5 | 80 | 199 | 403 |
| 4 (2250-56) | 512 HAU $10^{7.9}$ $EID_{50}$ 0.71 ug H5 | 24 | 1 | 96 | 527 | 640 |
| 5 (2250-57) | 1024 HAU $10^{8.2}$ $EID_{50}$ 1.42 ug H5 | 22 | 3 | 88 | 328 | 640 |
| 6 (N/A) | Nonvac | 0 | 25 | 0 | 5 | N/A |

-H5N3 (BPL inactivated) antigen stock 2228-90-15FEB05 used in all HAI testing
*nonresponders removed

TABLE 9

Serologic response and protection against mortality for individual birds administered serial 2285-26 (64 HAU/$10^{7.0}$ $EID_{50}$/0.09 ug H5 per dose)

| Bird ID # | HI titer | Mortality (+/−) | Reisolation |
|---|---|---|---|
| 401 | 20 | − | + |
| 402 | <10 | + | n.d. |
| 403 | <10 | + | n.d. |
| 404 | <10 | + | n.d. |
| 405 | 20 | n.d. | n.d. |
| 406 | 40 | n.d. | n.d. |
| 407 | ≥640 | − | − |
| 408 | 320 | − | − |
| 409 | 160 | − | − |
| 410 | ≥640 | − | − |
| 411 | 80 | − | − |
| 412 | ≥640 | − | − |
| 413 | ≥640 | − | − |
| 414 | ≥640 | − | − |
| 415 | ≥640 | n.d. | n.d. |
| 416 | 40 | − | + |
| 417 | ≥640 | − | − |
| 418 | 20 | n.d. | n.d. |
| 419 | 80 | − | − |
| 420 | ≥640 | − | − |
| 421 | 40 | − | − |
| 422 | ≥640 | − | − |
| 423 | ≥640 | n.d. | n.d. |
| 424 | ≥640 | − | − |
| 425 | <10 | + | n.d. | n.d. = not determined, bird not challenged or died before swabbing

TABLE 10

Serologic response and protection against mortality for individual birds administered serial 2285-21 (128 HAU/$10^{7.3}$ $EID_{50}$/0.18 ug H5 per dose).

| Bird ID # | HI titer | Mortality (+/−) | Reisolation |
|---|---|---|---|
| 226 | 320 | − | − |
| 227 | ≥640 | − | − |
| 228 | 320 | − | − |
| 229 | 160 | − | − |
| 230 | ≥640 | − | − |
| 231 | ≥640 | − | − |
| 232 | <10 | + | n.d. |
| 233 | <10 | n.d. | n.d. |
| 234 | <10 | + | n.d. |
| 235 | ≥640 | n.d. | n.d. |
| 236 | ≥640 | − | − |
| 237 | <10 | n.d. | n.d. |
| 238 | ≥640 | − | − |
| 239 | ≥640 | − | − |
| 240 | <10 | − | − |
| 241 | ≥640 | n.d. | n.d. |
| 242 | ≥640 | − | + |
| 243 | ≥640 | − | − |
| 244 | <10 | + | n.d. |
| 245 | ≥640 | n.d. | n.d. |
| 246 | ≥640 | − | − |
| 247 | ≥640 | − | − |
| 248 | ≥640 | − | − |
| 249 | ≥640 | − | − |
| 250 | 320 | − | − | n.d. = not determined, bird not challenged or died before swabbing

TABLE 11

Serologic response and protection against mortality for individual birds administered serial 2250-55 (256 HAU/$10^{7.6}$ $EID_{50}$/0.35 ug H5 per dose).

| Bird ID # | HI titer | Mortality (+/−) | Reisolation |
|---|---|---|---|
| 301 | ≥640 | − | − |
| 302 | ≥640 | − | − |
| 303 | 10 | − | + |
| 304 | <10 | + | n.d. |
| 305 | ≥640 | − | − |
| 306 | <10 | + | n.d. |
| 307 | ≥640 | n.d. | n.d. |
| 308 | 320 | − | − |
| 309 | ≥640 | n.d. | n.d. |
| 310 | ≥640 | − | − |
| 311 | ≥640 | − | − |
| 312 | ≥640 | − | − |

TABLE 11-continued

Serologic response and protection against mortality for individual birds administered serial 2250-55 (256 HAU/$10^{7.6}$ EID$_{50}$/0.35 ug H5 per dose).

| Bird ID # | HI titer | Mortality (+/−) | Reisolation |
|---|---|---|---|
| 313 | ≥640 | − | − |
| 314 | ≥640 | n.d. | n.d. |
| 315 | ≥640 | − | − |
| 316 | 40 | − | + |
| 317 | <10 | + | n.d. |
| 318 | <10 | + | n.d. |
| 319 | ≥640 | − | − |
| 320 | ≥640 | n.d. | n.d. |
| 321 | 80 | n.d. | n.d. |
| 322 | ≥640 | − | − |
| 323 | ≥640 | − | − |
| 324 | ≥640 | − | − |
| 325 | ≥640 | − | − | n.d. = not determined, bird not challenged or died before swabbing

TABLE 12

Serologic response and protection against mortality for individual birds administered serial 2250-56 (512 HAU/$10^{7.9}$ EID$_{50}$/0.71 ug H5 per dose).

| Bird ID # | HI titer | Mortality (+/−) | Reisolation |
|---|---|---|---|
| 276 | ≥640 | − | − |
| 277 | ≥640 | − | − |
| 278 | ≥640 | − | − |
| 279 | ≥640 | n.d. | n.d. |
| 280 | ≥640 | − | − |
| 281 | ≥640 | − | − |
| 282 | ≥640 | − | − |
| 283 | ≥640 | − | − |
| 284 | <10 | + | n.d. |
| 285 | ≥640 | n.d. | n.d. |
| 286 | ≥640 | − | − |
| 287 | ≥640 | − | − |
| 288 | ≥640 | − | − |
| 289 | ≥640 | − | − |
| 290 | ≥640 | n.d. | n.d. |
| 291 | ≥640 | − | − |
| 292 | ≥640 | − | − |
| 293 | ≥640 | n.d. | n.d. |
| 294 | ≥640 | − | − |
| 295 | ≥640 | − | − |
| 296 | ≥640 | − | − |
| 297 | ≥640 | − | − |
| 298 | ≥640 | n.d. | n.d. |
| 299 | ≥640 | − | − |
| 300 | ≥640 | − | − | n.d. = not determined, bird not challenged or died before swabbing

TABLE 13

Serologic response for individual birds administered serial 2250-57 (1024 HAU/$10^{8.2}$ EID$_{50}$/1.42 ug H5 per dose).

| Bird ID # | HI titer | Mortality (+/−) | Reisolation |
|---|---|---|---|
| 201 | ≥640 | n.d. | n.d. |
| 202 | ≥640 | n.d. | n.d. |
| 203 | ≥640 | n.d. | n.d. |
| 204 | ≥640 | n.d. | n.d. |
| 205 | ≥640 | n.d. | n.d. |
| 206 | ≥640 | n.d. | n.d. |
| 207 | ≥640 | n.d. | n.d. |
| 208 | ≥640 | n.d. | n.d. |
| 209 | ≥640 | n.d. | n.d. |
| 210 | <10 | n.d. | n.d. |
| 211 | <10 | n.d. | n.d. |
| 212 | ≥640 | n.d. | n.d. |
| 213 | ≥640 | n.d. | n.d. |
| 214 | ≥640 | n.d. | n.d. |
| 215 | ≥640 | n.d. | n.d. |
| 216 | ≥640 | n.d. | n.d. |
| 217 | ≥640 | n.d. | n.d. |
| 218 | ≥640 | n.d. | n.d. |
| 219 | ≥640 | n.d. | n.d. |
| 220 | ≥640 | n.d. | n.d. |
| 221 | <10 | n.d. | n.d. |
| 222 | ≥640 | n.d. | n.d. |
| 223 | ≥640 | n.d. | n.d. |
| 224 | ≥640 | n.d. | n.d. |
| 225 | ≥640 | n.d. | n.d. | n.d. = not determined, birds of this group not challenged

TABLE 14

Susceptibility to challenge induced mortality and lack of serologic response for individual birds on the nonvaccinated control group.

| Bird ID # | HI titer | Mortality (+/−) | Reisolation |
|---|---|---|---|
| 326 | <10 | + | n.d. |
| 327 | <10 | + | n.d. |
| 328 | <10 | + | n.d. |
| 329 | <10 | + | n.d. |
| 330 | <10 | + | n.d. |
| 331 | <10 | + | n.d. |
| 332 | <10 | + | n.d. |
| 333 | <10 | + | n.d. |
| 334 | <10 | + | n.d. |
| 335 | <10 | n.d. | n.d. |
| 336 | <10 | + | n.d. |
| 337 | <10 | n.d. | n.d. |
| 338 | <10 | + | n.d. |
| 339 | <10 | n.d. | n.d. |
| 340 | <10 | + | n.d. |
| 341 | <10 | + | n.d. |
| 342 | <10 | n.d. | n.d. |
| 343 | <10 | + | n.d. |
| 344 | <10 | + | n.d. |
| 345 | <10 | + | n.d. |
| 346 | <10 | n.d. | n.d. |
| 347 | <10 | + | n.d. |
| 348 | <10 | + | n.d. |
| 349 | <10 | + | n.d. |
| 350 | <10 | + | n.d | n.d. = not determined, bird not challenged or died before swabbing

The groups vaccinated with the inactivated prototypes (Groups 1-5) responded with geometric mean titer levels of 109, 174, 199, 527, and 328 respectively when results from all birds tested are considered. A number of birds had no measurable response, indicating they were misvaccinated or simply nonresponsive to vaccination. If those birds are removed from consideration, geometric mean titers for Groups 1-5 are 195, 533, 403, 640 and 640, respectively. Note that in calculation of geometric mean titers, a bird with no measurable response (<1:10, the lowest dilution tested) was analyzed as a titer of 5. For birds with a response recorded as 640 (the highest dilution tested) the actual endpoint may have been higher had testing been conducted to extinction, but these birds were nevertheless analyzed as a titer of 640. Geometric mean titers therefore are of limited value in assessment of the vaccines performance.

With respect to serologic response, for Groups 1-5 vaccinated with ascending dose levels, 18/25 (72%), 19/25 (76%), 20/25 (80%), 24/25 (96%) and 22/25 (88%) respectively, responded with a titer of 1:40 or greater.

The results of serologic testing were thus further evaluated on an individual bird basis and it was observed that several birds had no measurable post-vaccination antibody titer. In considering the results of the previous potency study in which the same vaccines were tested and found to be capable of inducing a solid antibody response, it is highly likely that misvaccination of the birds was a significant factor. Further explanation is provided in subsequent discussion of the results of challenge.

Challenge Protection

The results of this study are considered to demonstrate efficacy against mortality induced by virulent H5-type avian influenza challenge. As is clear from the summary data provided in Table 15, the highly pathogenic strain A/chicken/Vietnam/c58/04 (H5N1 type) of avian influenza induced mortality in 100% of nonvaccinated control chickens within two days of challenge administration. Meanwhile, all vaccinated groups were protected at a level of 80% or greater against mortality after the same challenge. The two vaccines that would have been deemed unsatisfactory for potency in this study were nevertheless demonstrated to be protective against challenge. This is considered to indicate the stringency of the potency test method in containing conservative criteria to confirm the ability of a batch under test to afford protection.

TABLE 15

Prevention of mortality induced by avian influenza A/chicken/Vietnam/c58/04 (H5N1 type) by inactivated rgH5N3 vaccines

| Treatment Group | Antigen/ dose | # mortalities/ # challenged | % mortality | Prevented fraction (95% CI) |
|---|---|---|---|---|
| 1 (2285-26) | 64 HAU $10^{7.0}$ EID$_{50}$ 0.09 ug H5 | 4/20 | 20% | 80% (56, 94.3) |
| 2 (2285-21) | 128 HAU $10^{7.3}$ EID$_{50}$ 0.18 ug H5 | 3/20 | 15% | 85% (62.1, 96.8) |
| 3 (2250-55) | 256 HAU $10^{7.6}$ EID$_{50}$ 0.35 ug H5 | 4/20 | 20% | 80% (56.3, 94.3) |
| 4 (2250-56) | 512 HAU $10^{7.9}$ EID$_{50}$ 0.71 ug H5 | 1/20 | 5% | 95% (75.1, 99.9) |
| 6 (N/A) | Nonvac | 20/20 | 100 | 0 |

Note:
Treatment group 5 was not challenged.

Virus reisolation from trachea and cloaca was also performed on swabs obtained from surviving chickens at four days post-challenge. As previously observed, post-challenge mortality in the nonvaccinated chickens was 100% such that it was not possible to determine reisolation in the control group, and therefore not possible to perform statistical assessment of protection against reisolation.

Because of the leg-band identification of each bird, serologic and protective response could be tracked on an individual bird basis as reported in Tables 9-14. Of particular interest is the resulting comparison between HAI titer measured by the standardized potency test and mortality and reisolation of virus after challenge. As summarized in Table 16, for those chickens with a negative antibody response of <10, mortality after challenge was a virtual certainty. For those chickens with a low antibody response of 10 to 40, mortality was completely prevented but viral shedding was not. For those chickens with an antibody response of 80 or greater, both mortality and shedding from trachea and/or cloaca were substantially prevented.

TABLE 16

Relationship between potency test titer (HAI) and protection against highly virulent H5N1 avian influenza in vaccinated and subsequently challenged birds irrespective of vaccine dose

| Titer group | # birds in titer group | # mortalities | # reisolation positive |
|---|---|---|---|
| <10 | 13 | 12/13 | 0/1 |
| 10-40 | 5 | 0/5 | 4/5 |
| >40 | 62 | 0/62 | 1/62 |

The prevented fraction for mortality for birds with measurable titer (≥1:10) compared to birds without measurable titer (<1:10) was 100% (95% CI 94.6, 100). The prevented fraction for mortality for birds with a titer >1:40 compared to birds with a titer <1:10 was 100% (95% CI 94.2, 100). There were insufficient numbers of birds with intermediate titer levels (1:10-1:40) to make statistical inferences of protection associated with such titers. Once again, a threshold value of 1:40 or greater in the vaccination/serology release assay would appear to be conservatively placed to ensure adequate confirmation of batch potency.

These results point to the critical importance of proper vaccine administration. Even the best vaccine, poorly administered such that chickens achieve suboptimal antibody response, can lead to birds that survive to shed virus. If for no other reason than this, for a vaccination program intended to prevent not just mortality but reduce shedding in birds exposed to high-path H5N1 avian influenza, a two dose regimen should be seriously considered. The field safety study to be conducted in support of conditional license will thus incorporate the use of two vaccinations.

Conclusion

Efficacy against mortality induced by highly pathogenic H5-type avian influenza has been demonstrated for inactivated vaccine containing the H5N3 strain at a dose of 64 HAU/107.0 EID$_{50}$/0.09 ug H5 per dose or greater.

Example 4

Efficacy of H5N3 Inactivated Influenze Vaccine in Ducks

Vaccines

Several vaccines were prepared, one of which was a placebo vaccine containing virus-free allantoic fluid. All remaining vaccines contained inactivated avian influenza viral stock prepared essentially as described in Example 1 and are described in Table 17. Inactivated antigen stock was prepared by one passage in Vero cells during construction of the reassortant virus, followed by six SPF egg passages.

Vaccines were formulated into a water-in-oil emulsion (60:40 oil:aqueous ratio) with mineral oil as the carrier and Tween 80 and Arlacel 83 as emulsifiers. The Tween and antigen components were mixed separately from the Drakeol and Arlacel 83, and the aqueous phase was added slowly to the oil phase whilst stirring to form a pre-emulsion. The pre-emulsion was then mechanically homogenized using a fixed-head Silverson L4R Homogenizer.

TABLE 17

| Vaccines Used | | | |
|---|---|---|---|
| | Avian influenza antigen content/dose | | |
| Vaccine serial | ug H5 | HAU | Used in Experiments |
| 2073-11 | 0.25 | 64 | 1, 2, 3 |
| 2073-12 | 0.50 | 128 | 1, 3 |
| 2073-13 | 1.20 | 307 | 1, 3 |
| 2073-14 | 0 | 0 | 1, 2, 3 |
| 2228-45 | 0.125 | 32 | 2, 3 |
| 2228-46 | 0.0625 | 16 | 2, 3 |
| 2228-51 | 0.0313 | 8 | 3 |

Vaccinations

Ducks (*Anas platyrhynchos*; from Ideal Poultry, Cameron, Tex.) were leg-banded prior to vaccination with records kept of assignment to treatment groups and pens. Ducks were vaccinated as indicated in Tables 18-20. Ducks in Experiment 1 were vaccinated intramuscularly in the breast, with 0.5 mL (Groups 1-3) or 0.6 mL (Group 4) using a 3 mL sterile disposable syringe fitted to a 20-gauge, ½"-¾" needle. Ducks in Group 5 remained nonvaccinated. Primary vaccination occurred when the ducks were 2 weeks of age, with a booster vaccination administered in the same manner when the birds were 5 weeks of age.

Ducks in Experiment 2 were vaccinated intramuscularly in the breast with 0.5 mL using a 3 mL sterile disposable syringe fitted to a 20-gauge, ½"-¾" needle. Primary vaccination occurred when the ducks were 2 weeks of age, with a booster vaccination administered in the same manner when the birds were 5 weeks of age.

Ducks in Experiment 3 were similarly vaccinated intramuscularly in the breast with 0.5 mL, with the exception of Group 8 which received 0.25 mL of serial #2228-51. Vaccination occurred when the ducks were 1 week of age and no booster vaccination was administered.

TABLE 18

| Table of Treatments - #1 | | | | |
|---|---|---|---|---|
| Treatment group | Vaccine | Vaccination | Challenge (8 weeks of age) | Virus shedding |
| 1 | Placebo (lot #2073-14) | At 2 and 5 weeks of age | A/chicken/ Vietnam/c58/04 | Tracheal and cloacal swabs at 3, 5, 10 and 17 days post-challenge |
| 2 | 0.25 ug/64 HAU (lot #2073-11) | | | |
| 3 | 0.5 ug/128 HAU (lot #2073-12) | | | |
| 4 | 1.2 ug/307 HAU (lot #2073-13) | | | |

TABLE 19

| Table of Treatments - #2 | | | | |
|---|---|---|---|---|
| Treatment group | Vaccine | Vaccination | Challenge (8 weeks of age) | Virus shedding |
| 1 | Placebo (lot #2073-14) | At 2 and 5 weeks of age | A/chicken/ Vietnam/c58/04 | Tracheal and cloacal swabs at 3, 5, 7, and 11 days post-challenge |
| 2 | 0.25 ug/64 HAU (lot #2073-11) | | | |
| 3 | 0.125 ug/32 HAU (lot #2228-45) | | | |
| 4 | 0.0625 ug/16 HAU (lot #2228-46) | | | |

TABLE 20

| Table of Treatments - #3 | | | | |
|---|---|---|---|---|
| Treatment group | Vaccine | Vaccination | Challenge (8-9 weeks of age) | Virus shedding |
| 1 | Placebo (lot #2073-14) | At 1 week of age | A/duck/Thailand/ D4AT/04 | Tracheal and cloacal swabs at 4, 7, and 11 days post-challenge |
| 2 | 1.2 ug/307 HAU (lot #2073-13) | | | |
| 3 | 0.5 ug/128 HAU (lot #2073-12) | | | |
| 4 | 0.25 ug/64 HAU (lot #2073-11) | | | |
| 5 | 0.125 ug/32 HAU (lot #2228-45) | | | |
| 6 | 0.0625 ug/16 HAU (lot #2228-46) | | | |

TABLE 20-continued

Table of Treatments - #3

| Treatment group | Vaccine | Vaccination | Challenge (8-9 weeks of age) | Virus shedding |
|---|---|---|---|---|
| 7 | 0.0313 ug/8 HAU (lot #2228-51) | | | |
| 8 | 0.015 ug/4 HAU (lot #2228-51, ½ volume dose) | | | |

Challenge

In Experiment 1 (see Table 18), challenge was conducted when the ducks reached 8 weeks of age. Ducks were administered the challenge virus A/chicken/Vietnam/c58/04 at 30 $CLD_{50}$ ($10^{4.5}$ $EID_{50}$) per duck when administered by intranasal instillation in a volume of 1.0 mL. All ducks were observed daily for mortality for at least 14 days post-challenge.

In Experiment 2 (see Table 19), challenge was conducted when the ducks reached 8 weeks of age. Ducks were administered the challenge virus A/chicken/Vietnam/c58/04 at 30 $CLD_{50}$ ($10^{4.5}$ $EID_{50}$) per duck when administered by intranasal instillation in a volume of 1.0 mL. All ducks were observed daily for mortality for at least 14 days post-challenge.

In Experiment 3 (see Table 20), challenge was conducted when the ducks reached 8-9 weeks (59 days) of age. Ducks were administered the challenge virus A/duck/Thailand/D4AT/04 at 100 $DLD_{50}$ ($10^{5.0}$ $EID_{50}$) per duck when administered by intranasal instillation in a volume of 1.0 mL.

All ducks were observed daily for mortality for at least 14 days post-challenge.

Sample Collection

Blood samples were collected from all birds at various time-points after vaccination and challenge. The blood was placed at 37 degrees C. for 30 minutes, then moved to 4 degrees C. overnight and allowed to clot. The serum was aseptically removed into separate sterile tubes for serologic analysis by hemagglutination inhibition assay. Sera samples were stored at −30 degrees Celsius or colder pending analysis.

At various time-points after challenge, tracheal and cloacal swabs were obtained from living birds for virus re-isolation in SPF chicken eggs. Swabs were placed in tubes containing 1 mL viral transport medium consisting of a 1:1 mix of PBS/Glycerol with $2\times10^6$ Units/L penicillin, $2\times10^6$ units/L polymixin B, 250 mg/L gentamicin, $0.5\times10^6$ units/L nystatin, 60 mg/L ofloxacin HCL and 0.2 gm/L sulfamethoxazole. Swabs were stored frozen at −70 degrees Celsius or colder pending analysis.

Efficacy of Vaccine in Experiment 1

A summary of the results of Experiment 1 is provided in Table 21.

TABLE 21

Efficacy of inactivated H5N3 influenza vaccines in ducks (Experiment 1)

| Treatment | Serology (HI GMT) | | | Trachea reisolation | | | | Cloaca reisolation | | | | Post- |
|---|---|---|---|---|---|---|---|---|---|---|---|---|
| Vaccine Dose | 21 dpv | 21 dpb | 25 dpc | 3 dpc | 5 dpc | 10 dpc | 17 dpc | 3 dpc | 5 dpc | 10 dpc | 17 dpc | challenge Mortality |
| 1.2 µg | 52 | 220 | 209 | 0/13 | 0/13 | 0/13 | 0/13 | 0/13 | 0/13 | 0/13 | 0/13 | 0/13 |
| 0.5 µg | 45 | 151 | 142 | 0/12 | 0/12 | 0/12 | 0/12 | 0/12 | 0/12 | 0/12 | 0/12 | 0/12 |
| 0.25 µg | 72 | 290 | 177 | 1/14 | 0/14 | 0/14 | 0/14 | 0/14 | 0/14 | 1/14 | 0/14 | 0/14 |
| Placebo | <10 | <10 | 127 | 12/13 | 3/13 | 0/12 | 0/12 | 11/13 | 2/13 | 0/12 | 0/12 | 1/13 | dpv = days post vaccination
dpb = days post boost
dpc = days post challenge

Each of the doses of vaccine (1.2 ug, 0.5 ug and 0.25 ug) induced measurable levels of antibody as detected by HI; geometric mean titers at 21 days after primary vaccination were 52, 45, and 72 respectively. After revaccination, titers rose to 220, 151 and 290, respectively. Meanwhile, the placebo group had no detectable antibody after primary or secondary vaccination. After challenge, there was a considerable rise in antibody titer in the placebo-vaccinated group, while antibody titers in the antigen vaccinated groups were unchanged.

No death or disease signs were observed in placebo (or vaccinated) ducks challenged with A/chicken/Vietnam/C58/04 (H5N1) virus. However, at three days post-challenge, virus was reisolated from all of the placebo vaccinated group while no virus was reisolated from any of the vaccinated groups.

Vaccine efficacy in preventing virus isolation from tracheal swabs was 100% (95% CI, 76.43%-100%), 100% (95% CI, 73.06%-100%) and 100% (95% CI, 74.86%-100%) for vaccine doses of 0.25, 0.5 and 1.2 respectively. Vaccine efficacy for preventing virus isolation from cloacal swabs was 100% (95% CI, 75.07%-100%), 100% (95% CI, 71.47%-100%), and 100% (95% CI, 73.39%-100%) for vaccine doses 0.25, 0.5 and 1.2 respectively.

Efficacy of Vaccine in Experiment 2

A summary of the results of Experiment 2 is provided in Table 22.

TABLE 22

Efficacy of inactivated H5N3 influenza vaccines in ducks (Experiment 2)

| Treatment Vaccine Dose | Serology (HI GMT) | | | Trachea reisolation | | | | Cloaca reisolation | | | | Post-challenge Mortality |
|---|---|---|---|---|---|---|---|---|---|---|---|---|
| | 21 dpv | 21 dpb | 21 dpc | 3 dpc | 5 dpc | 7 dpc | 11 dpc | 3 dpc | 5 dpc | 7 dpc | 11 dpc | |
| 0.25 µg (a) | 37 | 435 | 253 | 1/10 | 0/10 | 0/10 | 0/10 | 0/10 | 0/10 | 0/10 | 0/10 | 0/10 |
| 0.25 µg (b) | 35 | 367 | 367 | 0/10 | 0/10 | 0/10 | 0/10 | 0/10 | 0/10 | 0/10 | 0/10 | 0/10 |
| 0.125 µg | 15 | 211 | 171 | 1/10 | 0/10 | 0/10 | 0/10 | 0/10 | 0/10 | 1/10 | 0/10 | 0/10 |
| 0.0625 µg | 21 | 239 | 149 | 0/10 | 0/10 | 0/10 | 0/10 | 0/10 | 0/10 | 0/10 | 0/10 | 0/10 |
| 0.0313 µg | <10 | 92 | 121 | 0/10 | 0/10 | 0/10 | 0/10 | 0/10 | 0/10 | 0/10 | 0/10 | 0/10 |
| Placebo | <10 | <10 | 345 | 9/10 | 3/9 | 0/10 | 0/10 | 9/10 | 2/9 | 1/9 | 0/9 | 1/10 | dpv = days post vaccination
dpb = days post boost
dpc = days post challenge

Ducks in this experiment that received vaccines prepared at lower antigen content (0.0313, 0.0625 and 0.125 ug HA) than in the first experiment had geometric mean HI titers of <10, 21 and 15 respectively. The lowest dose of vaccine (0.0313) induced detectable HI response in only 5 of 10 ducks after primary vaccination. After vaccination with 0.0625 or 0.125 ug HA, 8/10 ducks in each group responded with detectable HI antibody. In the 0.25 ug group, all ten ducks responded to primary vaccination. Upon revaccination, all groups showed a marked increase in HI titers which ranged from 92 (0.0313) to 435 (0.25), while the placebo vaccinated group remained negative. After challenge, there was a considerable rise in antibody titer in the placebo-vaccinated group, while antibody titers in the antigen vaccinated groups were essentially unchanged.

After challenge, replication of challenge virus occurred only in the non-vaccinated control group in 10/10 birds. No virus replication was detected in ducks receiving two doses of 0.0313 or 0.0625 ug HA. In contrast, 2/10 ducks in the 0.125 ug group and 1 of 20 in the 0.25 ug group shed virus for one day at the lowest detectable level. The vaccine efficacy for prevention of tracheal shedding was 100% (95% CI, 68.05%-100%) after two doses of 0.0313 to 0.0625 ug, and 94.44% (95% CI, 73.5%-9.82%) after two doses of 0.25 ug in comparison to controls. The vaccine efficacy for prevention of tracheal shedding after two doses of 0.125 ug was 88.89% (95% CI, 51.87%-99.65%) compared to control ducks commingled in the same pens.

Efficacy of Vaccine in Experiment 3

The first two experiments used a prime-and-boost regimen, and all antigen levels tested induced protection against viral shed. Thus in the third experiment, a single vaccination with further reduced antigen content vaccines was tested.

TABLE 23

Efficacy of inactivated H5N3 influenza vaccines in ducks (Experiment 3)

| Treatment Vaccine Dose | Serology | | Trachea reisolation | | | Cloaca reisolation | | | Post-challenge Mortality |
|---|---|---|---|---|---|---|---|---|---|
| | Pre-chall | Post-chall | 4 dpc | 7 dpc | 11 dpc | 4 dpc | 7 dpc | 11 dpc | |
| 1.2 µg | 40 | 20 | 0/8 | 0/8 | 0/8 | 0/8 | 0/8 | 0/8 | 0/8 |
| 0.5 µg | 101 | 180 | 0/6 | 0/6 | 0/6 | 0/6 | 0/6 | 0/6 | 0/6 |
| 0.25 µg | 40 | 32 | 0/7 | 0/7 | 0/7 | 0/7 | 0/7 | 0/7 | 0/7 |
| 0.125 µg | 15 | 13 | 0/7 | 0/7 | 0/7 | 0/7 | 0/7 | 0/7 | 0/7 |
| 0.0625 µg | 14 | 11 | 0/8 | 0/8 | 0/8 | 0/8 | 0/8 | 0/8 | 0/8 |
| 0.0313 µg | <10 | <10 | 0/8 | 0/8 | 0/8 | 0/8 | 0/8 | 0/8 | 0/8 |
| 0.015 µg | <10 | <10 | 0/8 | 0/8 | 0/8 | 0/8 | 0/8 | 0/8 | 0/8 |
| Placebo | <10 | 135 | 12/12 | 2/6 | 0/6 | 8/12 | 0/6 | 0/6 | 8/12 | dpc = days post challenge

Pre-challenge antibody titers ranged from <10 (0.015 ug HA) to 101 (0.5 ug HA). The HI titer of antibody to challenge virus did not increase after challenge in the vaccinated groups of ducks, but did increase in the placebo-control group, indicating the challenge virus did not replicate in vaccinated ducks.

No mortality or disease signs were detected in any of the vaccinated ducks. In contrast, 8/12 of the placebo group died and the remaining had severe disease signs including neurologic abnormalities and/or cloudy eyes. Ducks were assigned to treatment group by pen, such that the effect of pen could not be excluded in statistical evaluation of differences in protection afforded by the vaccines tested. Nevertheless, statistical analysis of protection was conducted as based on the bird, with Bonferroni adjustments made to calculate p-values. Within this context, there was a significant prevention of mortality in pens of ducks vaccinated with the 1.2, 0.0625, 0.0313 or 0.015 ug doses of vaccine compared to ducks in control pens (p=0.0329), and the vaccine efficacy for these groups was 100% (95% CI, 34.94%-100%). The difference in mortality between pens of ducks vaccinated with the 0.125, 0.5 and 0.25 ug doses of vaccine compared to control pens was not statistically significant (p=0.0897). This likely reflects the low statistical power of the study as a result of the constraint in the number of ducks that can be accommodated in the BSL3+ facilities, and not necessarily the effectiveness of the vaccine at these doses. The vaccine efficacy for prevention of mortality in pens of ducks administered the 0.125 and 0.25 ug doses of vaccine was 100% (95% CI, 38.63%-100%) as compared to controls. The vaccine efficacy for the prevention of mortality in pens of ducks administered the 0.5 ug dose of vaccine was 100% (95% CI, 22.03%-100%) compared to controls.

Conclusion

All dose levels and/or vaccination regimens tested induced a protective response either in terms of prevention of mortality and/or in terms of prevention of virus shed from the trachea or cloaca. With respect to formulation, the use of a mineral oil based adjuvant system with Arlacel 83 and Tween 80 as emulsifiers, to provide a 60/40 oil:aqueous ratio emulsion, is demonstrated to be extremely effective in ducks. This emulsion has similarly proven very effective as a formulation for use in chickens, and in a related inactivated bivalent avian influenza product, Poulvac i-AI H5N9, H7N1 produced by FDAH in the Netherlands.

In Experiment 1, all dose levels were protective after two vaccinations, and Experiment 2 evaluated the use of lower dose levels in an effort to define a minimum dose necessary for protection. However, two vaccinations with even reduced antigen content vaccines were completely protective against viral shed after challenge. This yielded the study design for Experiment 3 in which single doses of vaccines, including one at yet further reduced antigen content, were evaluated, and a That isolate known to cause duck mortality was used for challenge.

Thus Experiment 3 represents the most rigorous testing conducted, in that ducks were administered a single dose of vaccine at one week of age, and were challenged at 8-9 weeks of age with an isolate highly pathogenic for waterfowl. In this model, a single vaccination with as little as 4 HAU of avian influenza antigen (½ volume dose of serial 2228-51) was demonstrated to be efficacious in preventing mortality and viral shed from trachea and cloaca. This experiment also demonstrated a duration of immunity of at least 7 weeks after administration of a single dose of vaccine.

Taken together, these three experiments indicate the effectiveness of the vaccine in ducks under two different scenarios. The first two experiments demonstrate the vaccine may be able to prevent a carrier state in ducks, as vaccinated ducks did not shed virus after challenge with an isolate that does not cause significant clinical signs or mortality in waterfowl but is highly pathogenic for chickens. The third experiment demonstrated the vaccine is able to prevent clinical signs, mortality and viral shedding in ducks after challenge with an isolate of known waterfowl pathogenicity.

The recommended vaccination regimen for this vaccine will incorporate the results of the experiments described in this report, an experiment conducted at CSIRO/AAHL (Australia), along with considerations appropriate to the epidemiology of avian influenza and common husbandry procedures for commercial duck production. That recommended regimen will be for a vaccine containing 256 HAU/0.5 mL (an antigen content well in excess of that demonstrated protective in this current report, and far less than that being used in safety studies), to be administered subcutaneously as a reduced volume day-of-age dose, followed by a full volume booster dose at 3 weeks of age (a regimen demonstrated effective in the referenced CSIRO study). By this regimen ducks may derive the benefit of an early vaccination, with a booster vaccination administered to convert any birds which may have been misvaccinated at day of age and/or boost the immune response to very high levels.

Example 4

Assessment of the Effect of Prior Immunization of Commercial Ducks and Inactivated Avian Influenze Vaccines on a Challenge with Highly Pathogenic Avian Influenza Virus Vaccine Preparation Infected allantoic fluid (passed twice in SPF chicken eggs) was diluted in sterile PBSA to provide a dose of the order of $10^{1.5}$ duck infectious doses$_{50}$ (DID$_{50}$) or $10^{4.7}$ egg infectious doses$_{50}$ (EID$_{50}$) per 0.5 ml. Back titration of the inoculum in SPF chicken eggs confirmed the titre of the virus in the challenge.

Vaccination

Sixty day-old commercial ducklings of Pekin origin were randomly divided into three groups, initially each of 20 birds. Pre-immunization screening of 10 ducklings was carried out by c-ELISA for antibody to avian influenza. Each duckling tested was negative for antibodies to avian influenza.

The three groups were managed as follows:

Group A: was vaccinated (Inactivated H5 vaccine Poulvac i-AI H5N9, H7N1) at 1 day old and 3 weeks old and then challenged at 6 weeks old by the intra-nasal (0.2 ml), intraocular (0.1 ml) and oral (0.2 ml) routes with 0.5 ml of a viral suspension H5N1 containing $10^{1.5}$ DID$_{50}$ ($10^{4.7}$ EID$_{50}$).

Group B: was vaccinated (Inactivated H5 vaccine Poulvac i-AI H5N3) at 1 day old and 3 weeks old and then challenged at 6 weeks old by the intra-nasal (0.2 ml), intraocular (0.1 ml) and oral (0.2 ml) routes with 0.5 ml of a viral suspension H5N1 containing $10^{1.5}$ DID$_{50}$ ($10^{4.7}$ EID$_{50}$).

Group C: was challenged at 6 weeks old by the intra-nasal (0.2 ml), intraocular (0.1 ml) and oral (0.2 ml) routes with 0.5 ml of a viral suspension H5N1 containing $10^{1.5}$ DID$_{50}$ ($10^{4.7}$ EID$_{50}$).

Day old vaccination was administered as a 0.2 ml dose given subcutaneously high on the neck. Revaccination at 3 weeks old was administered by subcutaneous vaccination of a 0.5 ml dose high on the neck.

Prior to challenge, group sizes were reduced to 15 birds per group (14 controls) and all birds were individually identified by means of a numbered leg band prior to challenge. Blood samples for serology studies were obtained from each duckling immediately prior to challenge and from each surviving duckling 11 and 14 days after challenge. Challenge was performed by means of a 1 ml graduated syringe. The inoculum was carefully introduced through one or both nares, into the open eyes, and into the mouth.

Birds were observed daily for clinical signs throughout the study and twice daily during periods of acute disease. In order to monitor virus shedding after challenge, tracheal and cloacal swabs from each challenged bird were obtained on days 4, 5, 6, and 7 post-challenge. Selected samples were subsequently used for virus isolation in SPF chicken eggs or commercial eggs (if SPF eggs were not available).

Mortality and Morbidity

By day 4 following challenge, all the control birds (Group C) had become depressed and inappetant, with green diarrhea and apparent weight loss. By day 10, 4 control birds had died without clinical signs and 5 others had been euthanased with neurological signs (twitching, head tilt, head bobbing, wing paralysis) leaving 5 birds remaining from this group from 14.

All 15 birds in each of the two vaccinated groups (Groups A and B) remained clinically well throughout the study period.

Serology

Blood in a quantity sufficient to perform all serologic tests was collected from the jugular or wing vein by puncture. Sera was harvested and stored at −20 degrees Celsius or lower until they were tested.

All non-vaccinated birds were negative for HI activity against the Vietnamese H5 antigen prior to challenge with H5N1 virus. Interestingly, there was a difference in post-vaccinal pre-challenge HI titres between the two groups of vaccinated birds, with the Group B H5N3 birds (n=15) having higher titres (1:8 to 1:64) than Group A which had been given the bivalent vaccine (n=15) (neg to 1:8).

The 5 surviving control birds in Group C clearly seroconverted to the challenge with day 11 titres ranging from 1:32 and 1:256 and day 14 titres ranging from 1:64 to 1:128.

Most birds in Group A (bivalent vaccine) had not seroconverted to the Vietnamese H5 prior to challenge but 6 of these seroconverted by day 11 and most had seroconverted by day 14 (1:32 and 1:128). Two birds which had detectable pre-challenge HI titres were one doubling dilution away from seroconversion by day 14. This suggests that viral replication within these 2 animals might have been inhibited to a slightly greater degree than other members of the cohort, and that seroconversion might be taking place a few days later than in non-immunized birds. Seroloby at a later time post-challenge would have been necessary to confirm this.

In Group B (reverse genetics vaccine), all birds had seroconverted to the Vietnamese H5 prior to challenge. However, no bird exhibited a rising titre after challenge suggesting that viral infection was not established in this group of ducks.

Virus Shedding

Tracheal and cloacal swabs from each challenged bird were obtained on days 4, 5, 6, and 7 post-challenge. After collecting tracheal and cloacal samples, samples were placed in isotonic phosphate buffered saline (PBS), pH 7.0-7.4, containing antibiotics. Suspensions were stored at −80 degrees Celsius prior to egg inoculation.

Virus isolation was performed in SPF embryonated fowl eggs except were indicated. The supernatant fluids of the samples collected on days 4 and 7 post-challenge were inoculated into the allantoic sac of at least three embryonated fowl eggs of 9-11 days incubation. The eggs were incubated at 35-37 degrees Celsius up to 5 days. Allantoic fluids from eggs containing dead or dying embryos as they arose, and all eggs remaining at the end of the incubation period were tested for haemagglutination (HA) activity. All allantoic fluids with haemagglutination activity were considered positive for the presence of the administered AI virus.

Group C: Avian influenza virus was reisolated from the trachea swab of each control bird on either day 4 or day 7 following challenge, and from the cloacal swab of 2 of these on day 4. These observations are consistent with those found in ducks administered the equivalent challenge dose in a previous titration study.

Group A: Avian influenza virus was reisolated on day 4 from the trachea of 2 birds vaccinated with the bivalent vaccine, and from the cloacal swab of one of these also on day 4. Virus was not reisolated from any bird in this group on day 7 following challenge.

Group B: Avian influenza virus was not reisolated from the trachea of cloacal swabs of any bird vaccinated with the reverse genetics H5N3 vaccine on either day 4 or day 7 following challenge.

Conclusion

High levels of morbidity (100%) and mortality (65%) were observed in the control group of ducks. Together with viral shedding and seroconversion of survivors, this indicates that the challenge virus as administered was capable of infecting and causing disease in naïve commercial ducks.

Vaccination with the bivalent inactivated H5 vaccine Poulvac i-AI H5N9, H7N1 did not lead to seroconversion of most ducks in the group to the Vietnamese H5, but did protect ducks from development of disease signs attributable to avian influenza. Most ducks seroconverted to the H5 following challenge, suggesting that viral replication had occurred in this group of birds. This interpretation of the serology is supported by reisolation of AI virus from some of these birds.

Vaccination with the inactivated H5 vaccine Poulvac i-AI H5N3 lead to seroconversion of all birds against the Vietnamese H5, and gave protection from morbidity following challenge with H5N1 virus. This group of birds did not seroconvert following viral challenge suggesting that viral replication had been suppressed in each of these birds. This is supported by failure to reisolate AI virus from any of the tracheal or cloacal swabs collected on either day 4 or day 7.

Example 5

Composition of Vaccine

The adjuvant was chosen based on the well-established immunostimulating effect of mineral oil emulsions, formulated as water in oil (W/O) emulsions. A pharmaceutical grade light mineral oil (NF) Drakeoil 5 may be used in the formulation.

In order to achieve a stable water-in-oil emulsion (W/O), surfactants may be used. The surfactants Sorbitan Sesquioleate (vegetable), a hydrophobic surfactant, and Polysorbate 80 (vegetable), a hydrophilic surfactant, are chosen because of their emulsifying properties. The use of a combination of these surfactants has now been shown to result in a stable emulsion.

Arlacel 83V=Sorbitan sesquioleate, an equimolar mixture of monoesters and diesters;

CAS number=8007-43-9. It is used in the preparations of creams, emulsions and ointments.

Tween 80V=Polysorbate 80=Polyoxyethylene 20 sorbitan monooleate;

CAS number=9005-65-6. It is used in the preparation of stable oil-in-water emulsions.

Sorbitan esters like Arlacel 83V produce stable W/O emulsions but are frequently used in combination with varying proportions of a polysorbate like Tween 80V to produce a W/O emulsion.

Both the Arlacel 83V and Tween 80V used to formulate the product are of vegetable origin.

The adjuvant was chosen based on the well-established immunostimulating effect of mineral oil emulsions, formulated as water in oil (W/O) emulsion. A pharmaceutical grade light mineral oil (NF) Drakeoil 5 is used in the formulation.

In order to achieve a stable water-in-oil emulsion (W/O), it is necessary to use surfactants. The surfactants Sorbitan Sesquioleate (vegetable), a hydrophobic surfactant, and Polysorbate 80 (vegetable), a hydrophilic surfactant, were chosen because of their emulsifying properties. The use of a combination of these surfactants has now been shown to result in a stable emulsion.

Arlacel 83V=Sorbitan sesquioleate, an equimolar mixture of monoesters and diesters;

CAS number=8007-43-9. It is used in the preparations of creams, emulsions and ointments.

Tween 80V=Polysorbate 80=Polyoxyethylene 20 sorbitan monooleate;

CAS number=9005-65-6. It is used in the preparation of stable oil-in-water emulsions.

Sorbitan esters like Arlacel 83V produce stable W/O emulsions but are frequently used in combination with varying proportions of a polysorbate like Tween 80V to produce a W/O emulsion.

Both the Arlacel 83V and Tween 80V used to formulate the product are of vegetable origin.

The dose volume of 0.5 ml is common for use in the poultry industry.

TABLE 24

COMPOSITION OF THE PRODUCT (per dose)

| Name of ingredient | Quantity | Function |
|---|---|---|
| Active ingredient(s) | | |
| Inactivated Avian Influenza Virus H5N3 RG | ≥128 HA | active ingredient |
| Constituents of the adjuvants | | |
| Light Mineral Oil | 230 mg | adjuvant |
| sorbitan sesquioleate (vegetable) | 22.5 mg | emulsifier |
| Polysorbate 80 (vegetable) | 4.3 mg | emulsifier |
| Constituents of the excipients | | |
| Thiomersal | 0.02 mg | preservative |
| Phosphate Buffered Saline | Ad 0.5 ml | diluent |

Example 6

The efficacy of graded doses of an inactivated avian influenza vaccine was tested. Formalin inactivated reassortant H5N3 virus was formulated into prototype water-in-oil emulsions at 0.25 ug hemagglutinin (HA) protein/dose, 0.5 ug HA protein/dose or 1.2 ug HA protein/dose. The associated dose levels of these vaccines in terms of hemagglutinating units (HAU) were 64, 128 and 307 HAU/dose respectively. The vaccine prototypes were administered intramuscularly to groups of 25 SPF White Leghorn chickens at two and five weeks of age. An antigen free placebo vaccine was similarly administered intramuscularly to a group of 25 hatchmates and an additional 25 hatchmates were left as nonvaccinated controls.

Just prior to the initial vaccination and at three weeks after the vaccinations, blood samples were obtained from the chickens for determination of avian influenza antibody titers by hemagglutination inhibition (HI) assay. Pre-bleed serum samples were all negative. Serum samples from all vaccinated groups obtained at 21 days post-primary vaccination and 21 days after booster vaccination contained high levels of antibody.

At three weeks after the booster vaccination, the chickens were challenged with a highly pathogenic H5N1 avian influenza isolate from Vietnam. The vaccines afforded 100% protection against mortality. Challenge virus reisolation from tracheal and cloacal swabs obtained from all living birds at various timepoints after challenge was minimal.

Chickens were wing-banded prior to vaccination and the wing-bands were randomized for assignment to treatment groups and pens. Chickens were vaccinated intramuscularly in the breast. Primary vaccination occurred when the chickens were 2 weeks of age, with a booster vaccination administered in the same manner when the birds were 5 weeks of age.

Challenge was conducted when the chickens reached 8 weeks of age. Chickens were administered the challenge virus A/chicken/Vietnam/c58/04, by intranasal/intratracheal instillation in a volume of 1.0 mL.

Blood samples were collected from all birds at 2, 5, 8 and 10-11 weeks of age. At 3, 5, 7, 10 and 14 days post challenge, tracheal and cloacal swabs were obtained from living birds for virus re-isolation in SPF eggs.

Methods for serum antibody quantitation and virus reisolation were per standard procedures.

For the claim of prevention of mortality, the study was originally designed to evaluate a primary outcome in terms of the occurrence of mortality, testing the null hypothesis that there was no difference in mortality among groups. Mortality was to be compared among groups in a generalized estimating equation model with mortality (0 or 1) as the dichotomous dependent variable and treatment included as an independent variable. If necessary the pen location would be included as a covariate in the model. As the nonvaccinated groups suffered 100% mortality and the vaccinated groups suffered no mortality, a chi-square analysis was used to calculate prevented fraction and it's associated confidence interval.

For the claim of prevention of virus shedding, the study was designed to evaluate a primary outcome in terms of the occurrence of virus isolation, testing the null hypothesis that there was no difference in the prevalence of virus isolation among groups. As described below, the almost total mortality in the nonvaccinated and placebo vaccinated control groups precluded any statistical analysis of re-isolation results and thus none was performed.

After vaccination of SPF chickens at two weeks and five weeks of age with the tested prototypes, high levels of antibody were measured by hemagglutination inhibition testing, and complete protection against challenge mortality was observed. There was minimal virus reisolation from vaccinated chickens after challenge, and while it cannot be stated there was a significant reduction in reisolation rates compared to controls (because all controls died before reisolation could be assessed in those groups), it is clear that the vaccine is capable of inducing significant reduction of shedding. For unequivocal proof of same, it would be necessary to modify the challenge protocol such that non-vaccinated or placebo vaccinated chickens do not immediately die after challenge. This may prove difficult as the H5N1 challenge strain is exceedingly pathogenic in chickens.

Three different antigen levels of this whole-virus inactivated vaccine were tested. Results were essentially the same for all three antigen levels, such that a minimum protective dose was not determined in this study. Further work with vaccines formulated to contain less than 0.25 ug (64 HAU)/dose of antigen will be necessary to determine the minimum. At the current time, it can be concluded that two vaccinations with a water-in-oil adjuvanted emulsion, containing the H5N3 reassortant virus at no less than 0.25 ug (64 HAU)/dose, is highly efficacious in preventing mortality induced by the H5N1 Vietnam virulent field isolate, and is also likely to be effective in preventing shed of virulent H5N1.

While the invention has been descried in each of its various embodiments, it is expected that certain modifications thereto may be undertaken and effected by the person skilled in the art without departing from the true spirit and scope of the invention, as set forth in the previous description and as further embodied in the following claims. The present invention is not to be limited in scope by the specific embodiments described herein. Indeed, various modifications of the invention in addition to those described herein will become apparent to those skilled in the art from the foregoing description and the accompanying figures. Such modifications are intended to fall within the scope of the appended claims. It is further to be understood that all values are approximate, and are provided for description. All patents and patent applications cited herein are hereby incorporated herein by reference in their entireties.

What is claimed is:

1. A vaccine composition which comprises a reassortant influenza virus, said virus consists of the following genomic segments: the HA from influenza virus A/chicken/Vietnam/C58/04 H5N1, the NA from influenza virus A/DK/Germany/1215/73 H2N3, and the PB1, PB2, PA, NP, M, and NS from influenza virus A/Puerto Rico/8/34 H1N1, adjuvanted in a water-in-oil emulsion, wherein the HA total is between 10 ng/dose to 1 ug/dose of said vaccine composition, and the water-in-oil emulsion comprises one or more sorbitan oleate esters.

2. The vaccine composition of claim 1, wherein the reassortant influenza virus is inactivated.

3. The vaccine composition of claim 1, wherein the sorbitan oleate esters are polysorbate 80 and sorbitan sesquioleate ester.

4. A method of incuding an immune response against influenza H5N3 in a poultry member, which comprises administering to the poultry member a vaccine composition as in any one of claims 1, 2 or 3.

5. The method of claim 4, wherein said vaccine composition is administered via drinking water or spraying.

6. The method of claim 4, wherein dosing is within the range of about 0.25 mL to 2.0 mL per poultry member.

7. The method of claim 6, wherein said vaccine is administered in no more than one dose.

8. A vaccine composition which comprises a reassortant influenza virus, said virus consists of the following genomic segments: the HA from influenza virus A/chicken/Vietnam/C58/04 H5N1, the NA from influenza virus A/DK/Germany/1215/73 H2N3, and the PB1, PB2, PA, NP, M and NS from influenza virus A/Puerto Rico/8/34 H1N1, adjuvanted with a biologically acceptable adjuvant material, wherein the HA total is between 10 ng/dose to 1 ug/dose of said vaccine composition, and also wherein said composition contains two surfactants consisting essentially of sorbitan oleate esters.

9. The vaccine composition of claim 8, wherein said surfactants are polysorbate 80 and sorbitan sesquinoleate ester.

10. The vaccine composition of claim 8, wherein the reassortant influenza virus is inactivated.

11. The vaccine composition of claim 8, further comprising at least one antigen.

\* \* \* \* \*

```
                              SEQUENCE LISTING

<160> NUMBER OF SEQ ID NOS: 21

<210> SEQ ID NO 1
   <211> LENGTH: 548
   <212> TYPE: PRT
   <213> ORGANISM: goose

<400> SEQUENCE: 1

Asp Gln Ile Cys Ile Gly Tyr His Ala Asn Asn Ser Thr Glu Gln Val
   1               5                   10                  15

Asp Thr Ile Met Glu Lys Asn Val Thr Val Thr His Ala Gln Asp Ile
                   20                  25                  30

Leu Glu Lys Thr His Asn Gly Lys Leu Cys Asp Leu Asp Gly Val Lys
                   35                  40                  45

Pro Leu Ile Leu Arg Asp Cys Ser Val Ala Gly Trp Leu Leu Gly Asn
   50                  55                  60

Pro Met Cys Asp Glu Phe Ile Asn Val Pro Glu Trp Ser Tyr Ile Val
   65                  70                  75                  80

Glu Lys Ala Ser Pro Ala Asn Asp Leu Cys Tyr Pro Gly Asp Phe Asn
                   85                  90                  95

Asn Tyr Glu Glu Leu Lys His Leu Leu Ser Arg Thr Asn His Phe Glu
                   100                 105                 110

Lys Ile Gln Ile Ile Pro Lys Ser Ser Trp Ser Asn His Asp Ala Ser
                   115                 120                 125

Ser Gly Val Ser Ser Ala Cys Pro Tyr His Gly Lys Ser Ser Phe Phe
                   130                 135                 140

Arg Asn Val Val Trp Leu Ile Lys Lys Asn Ser Ala Tyr Pro Thr Ile
   145                 150                 155                 160

Lys Arg Ser Tyr Asn Asn Thr Asn Gln Glu Asp Leu Leu Val Leu Trp
                   165                 170                 175

Gly Ile His His Pro Asn Asp Ala Ala Glu Gln Thr Lys Leu Tyr Gln
                   180                 185                 190

Asn Pro Thr Thr Tyr Ile Ser Val Gly Thr Ser Thr Leu Asn Gln Arg
                   195                 200                 205

Leu Val Pro Glu Ile Ala Thr Arg Pro Lys Val Asn Gly Gln Ser Gly
                   210                 215                 220

Arg Met Glu Phe Phe Trp Thr Ile Leu Lys Pro Asn Asp Ala Ile Asn
   225                 230                 235                 240

Phe Glu Ser Asn Gly Asn Phe Ile Ala Pro Glu Tyr Ala Tyr Lys Ile
                   245                 250                 255

Val Lys Lys Gly Asp Ser Ala Ile Met Lys Ser Glu Leu Glu Tyr Gly
                   260                 265                 270

Asn Cys Asn Thr Lys Cys Gln Thr Pro Met Gly Ala Ile Asn Ser Ser
                   275                 280                 285

Met Pro Phe His Asn Ile His Pro Leu Thr Ile Gly Glu Cys Pro Lys
                   290                 295                 300

Tyr Val Lys Ser Asn Arg Leu Val Leu Ala Thr Gly Leu Arg Asn Thr
   305                 310                 315                 320

Pro Gln Ile Glu Thr Arg Gly Leu Phe Gly Ala Ile Ala Gly Phe Ile
                   325                 330                 335
```

```
Glu Gly Gly Trp Gln Gly Met Val Asp Gly Trp Tyr Gly Tyr His His
            340                 345                 350

Ser Asn Glu Gln Gly Ser Gly Tyr Ala Ala Asp Lys Glu Ser Thr Gln
        355                 360                 365

Lys Ala Ile Asp Gly Val Thr Asn Lys Val Asn Ser Ile Ile Asp Lys
    370                 375                 380

Met Asn Thr Gln Phe Glu Ala Val Gly Arg Glu Phe Asn Asn Leu Glu
385                 390                 395                 400

Arg Arg Ile Glu Asn Leu Asn Lys Lys Met Glu Asp Gly Phe Leu Asp
                405                 410                 415

Val Trp Thr Tyr Asn Ala Glu Leu Leu Val Leu Met Glu Asn Glu Arg
    420                 425                 430

Thr Leu Asp Phe His Asp Ser Asn Ala Lys Asn Leu Tyr Asp Lys Val
            435                 440                 445

Arg Leu Gln Leu Arg Asp Asn Ala Lys Glu Leu Gly Asn Gly Cys Phe
    450                 455                 460

Glu Phe Tyr His Lys Cys Asp Asn Glu Cys Met Glu Ser Val Lys Asn
465                 470                 475                 480

Gly Thr Tyr Asp Tyr Pro Gln Tyr Ser Glu Glu Ala Arg Leu Asn Arg
                485                 490                 495

Glu Glu Ile Ser Gly Val Lys Leu Glu Ser Met Gly Thr Tyr Gln Ile
            500                 505                 510

Leu Ser Ile Tyr Ser Thr Val Ala Ser Ser Leu Ala Leu Ala Ile Met
        515                 520                 525

Val Ala Gly Leu Ser Leu Trp Met Cys Ser Asn Gly Ser Leu Gln Cys
    530                 535                 540

Arg Ile Cys Ile
545

<210> SEQ ID NO 2
<211> LENGTH: 548
<212> TYPE: PRT
<213> ORGANISM: chicken

<400> SEQUENCE: 2

Asp Gln Ile Cys Ile Gly Tyr His Ala Asn Asn Ser Thr Glu Gln Val
1               5                   10                  15

Asp Thr Ile Met Glu Lys Asn Val Thr Val Thr His Ala Gln Asp Ile
            20                  25                  30

Leu Glu Lys Thr His Asn Gly Lys Leu Cys Asp Leu Asp Gly Val Lys
        35                  40                  45

Pro Leu Ile Leu Arg Asp Cys Ser Val Ala Gly Trp Leu Leu Gly Asn
    50                  55                  60

Pro Met Cys Asp Glu Phe Ile Asn Val Pro Glu Trp Ser Tyr Ile Val
65                  70                  75                  80

Glu Lys Ala Asn Pro Val Asn Asp Leu Cys Tyr Pro Gly Asp Phe Asn
                85                  90                  95

Asp Tyr Glu Glu Leu Lys His Leu Leu Ser Arg Ile Asn His Phe Glu
            100                 105                 110

Lys Ile Gln Ile Ile Pro Lys Ser Ser Trp Ser Ser His Glu Ala Ser
        115                 120                 125

Leu Gly Val Ser Ser Ala Cys Pro Tyr Gln Gly Lys Ser Ser Phe Phe
    130                 135                 140

Arg Asn Val Val Trp Leu Ile Lys Lys Asn Ser Thr Tyr Pro Thr Ile
```

```
            145                 150                 155                 160
        Lys Arg Ser Tyr Asn Asn Thr Asn Gln Glu Asp Leu Leu Val Leu Trp
                        165                 170                 175
        Gly Ile His His Pro Asn Asp Ala Ala Glu Gln Thr Lys Leu Tyr Gln
                        180                 185                 190
        Asn Pro Thr Thr Tyr Ile Ser Val Gly Thr Ser Thr Leu Asn Gln Arg
                        195                 200                 205
        Leu Val Pro Arg Ile Ala Thr Arg Ser Lys Val Asn Gly Gln Ser Gly
                210                 215                 220
        Arg Met Glu Phe Phe Trp Thr Ile Leu Arg Pro Asn Asp Ala Ile Asn
        225                 230                 235                 240
        Phe Glu Ser Asn Gly Asn Phe Ile Ala Pro Glu Tyr Ala Tyr Lys Ile
                        245                 250                 255
        Val Lys Lys Gly Asp Ser Thr Ile Met Lys Ser Glu Leu Glu Tyr Gly
                        260                 265                 270
        Asn Cys Asn Ala Lys Cys Gln Thr Pro Met Gly Ala Ile Asn Ser Ser
                        275                 280                 285
        Met Pro Phe His Asn Ile His Pro Leu Thr Ile Gly Glu Cys Pro Lys
                290                 295                 300
        Tyr Val Lys Ser Asn Arg Leu Val Leu Ala Thr Gly Leu Arg Asn Ser
        305                 310                 315                 320
        Pro Gln Ile Glu Thr Arg Gly Leu Phe Gly Ala Ile Ala Gly Phe Ile
                        325                 330                 335
        Glu Gly Gly Trp Gln Gly Met Val Asp Gly Trp Tyr Gly Tyr His His
                        340                 345                 350
        Ser Asn Glu Gln Gly Ser Gly Tyr Ala Ala Asp Lys Glu Ser Thr Gln
                        355                 360                 365
        Lys Ala Ile Asp Gly Val Thr Asn Lys Val Asn Ser Ile Ile Asp Lys
                        370                 375                 380
        Met Asn Thr Gln Phe Glu Ala Val Gly Arg Glu Phe Asn Asn Leu Glu
        385                 390                 395                 400
        Arg Arg Ile Glu Asn Leu Asn Lys Lys Met Glu Asp Gly Phe Leu Asp
                        405                 410                 415
        Val Trp Thr Tyr Asn Ala Glu Leu Leu Val Leu Met Glu Asn Glu Arg
                        420                 425                 430
        Thr Leu Asp Phe His Asp Ser Asn Val Lys Asn Leu Tyr Asp Lys Val
                        435                 440                 445
        Arg Leu Gln Leu Arg Asp Asn Ala Lys Glu Leu Gly Asn Gly Cys Phe
                450                 455                 460
        Glu Phe Tyr His Lys Cys Asp Asn Glu Cys Met Glu Ser Val Arg Asn
        465                 470                 475                 480
        Gly Thr Tyr Asp Tyr Pro Gln Tyr Ser Glu Glu Ala Arg Leu Lys Arg
                        485                 490                 495
        Glu Glu Ile Ser Gly Val Lys Leu Glu Ser Ile Gly Ile Tyr Gln Ile
                        500                 505                 510
        Leu Ser Ile Tyr Ser Thr Val Ala Ser Ser Leu Val Leu Ala Ile Met
                        515                 520                 525
        Val Ala Gly Leu Ser Leu Trp Met Cys Ser Asn Gly Ser Leu Gln Cys
                530                 535                 540
        Arg Ile Cys Ile
        545

<210> SEQ ID NO 3
```

```
<211> LENGTH: 12
<212> TYPE: DNA
<213> ORGANISM: artificial sequence
<220> FEATURE:
<223> OTHER INFORMATION: primer

<400> SEQUENCE: 3
agcaaaagca gg                                                              12

<210> SEQ ID NO 4
<211> LENGTH: 28
<212> TYPE: DNA
<213> ORGANISM: artificial sequence
<220> FEATURE:
<223> OTHER INFORMATION: primer

<400> SEQUENCE: 4
tattggtctc agggagcgaa agcaggtc                                             28

<210> SEQ ID NO 5
<211> LENGTH: 34
<212> TYPE: DNA
<213> ORGANISM: artificial sequence
<220> FEATURE:
<223> OTHER INFORMATION: primer

<400> SEQUENCE: 5
atatggtctc gtattagtag aaacaaggtc gttt                                      34

<210> SEQ ID NO 6
<211> LENGTH: 28
<212> TYPE: DNA
<213> ORGANISM: artificial sequence
<220> FEATURE:
<223> OTHER INFORMATION: primer

<400> SEQUENCE: 6
tattcgtctc agggagcgaa agcaggca                                             28

<210> SEQ ID NO 7
<211> LENGTH: 33
<212> TYPE: DNA
<213> ORGANISM: artificial sequence
<220> FEATURE:
<223> OTHER INFORMATION: primer

<400> SEQUENCE: 7
atatcgtctc gtattagtag aaacaaggca ttt                                       33

<210> SEQ ID NO 8
<211> LENGTH: 29
<212> TYPE: DNA
<213> ORGANISM: artificial sequence
<220> FEATURE:
<223> OTHER INFORMATION: primer

<400> SEQUENCE: 8
tattcgtctc agggagcgaa agcaggtac                                            29

<210> SEQ ID NO 9
<211> LENGTH: 33
<212> TYPE: DNA
<213> ORGANISM: artificial sequence
<220> FEATURE:
<223> OTHER INFORMATION: primer

<400> SEQUENCE: 9
```

```
atatcgtctc gtattagtag aaacaaggta ctt                              33

<210> SEQ ID NO 10
<211> LENGTH: 28
<212> TYPE: DNA
<213> ORGANISM: artificial sequence
<220> FEATURE:
<223> OTHER INFORMATION: primer

<400> SEQUENCE: 10
tattcgtctc agggagcaaa agcagggg                                    28

<210> SEQ ID NO 11
<211> LENGTH: 35
<212> TYPE: DNA
<213> ORGANISM: artificial sequence
<220> FEATURE:
<223> OTHER INFORMATION: primer

<400> SEQUENCE: 11
atatcgtctc gtattagtag aaacaagggt gtttt                            35

<210> SEQ ID NO 12
<211> LENGTH: 37
<212> TYPE: DNA
<213> ORGANISM: artificial sequence
<220> FEATURE:
<223> OTHER INFORMATION: primer

<400> SEQUENCE: 12
attacgtctc tcctcttgtc tcaatttgag gggtatt                          37

<210> SEQ ID NO 13
<211> LENGTH: 36
<212> TYPE: DNA
<213> ORGANISM: artificial sequence
<220> FEATURE:
<223> OTHER INFORMATION: primer

<400> SEQUENCE: 13
attacgtctc agaggactat ttggggctat agcagg                           36

<210> SEQ ID NO 14
<211> LENGTH: 29
<212> TYPE: DNA
<213> ORGANISM: artificial sequence
<220> FEATURE:
<223> OTHER INFORMATION: primer

<400> SEQUENCE: 14
tattcgtctc agggagcaaa agcagggta                                   29

<210> SEQ ID NO 15
<211> LENGTH: 36
<212> TYPE: DNA
<213> ORGANISM: artificial sequence
<220> FEATURE:
<223> OTHER INFORMATION: primer

<400> SEQUENCE: 15
atatcgtctc gtattagtag aaacaagggt atttt                            36

<210> SEQ ID NO 16
<211> LENGTH: 29
<212> TYPE: DNA
```

```
<213> ORGANISM: artificial sequence
<220> FEATURE:
<223> OTHER INFORMATION: primer

<400> SEQUENCE: 16
tattggtctc agggagcaaa agcaggagt                                              29

<210> SEQ ID NO 17
<211> LENGTH: 36
<212> TYPE: DNA
<213> ORGANISM: artificial sequence
<220> FEATURE:
<223> OTHER INFORMATION: primer

<400> SEQUENCE: 17
atatggtctc gtattagtag aaacaaggag tttttt                                      36

<210> SEQ ID NO 18
<211> LENGTH: 29
<212> TYPE: DNA
<213> ORGANISM: artificial sequence
<220> FEATURE:
<223> OTHER INFORMATION: primer

<400> SEQUENCE: 18
tattcgtctc agggagcaaa agcaggtag                                              29

<210> SEQ ID NO 19
<211> LENGTH: 36
<212> TYPE: DNA
<213> ORGANISM: artificial sequence
<220> FEATURE:
<223> OTHER INFORMATION: primer

<400> SEQUENCE: 19
atatcgtctc gtattagtag aaacaaggta gttttt                                      36

<210> SEQ ID NO 20
<211> LENGTH: 29
<212> TYPE: DNA
<213> ORGANISM: artificial sequence
<220> FEATURE:
<223> OTHER INFORMATION: primer

<400> SEQUENCE: 20
tattcgtctc agggagcaaa agcagggtg                                              29

<210> SEQ ID NO 21
<211> LENGTH: 35
<212> TYPE: DNA
<213> ORGANISM: artificial sequence
<220> FEATURE:
<223> OTHER INFORMATION: primer

<400> SEQUENCE: 21
atatcgtctc gtattagtag aaacaagggt gtttt                                       35
```